US007910332B2

(12) United States Patent
Nielsen et al.

(10) Patent No.: US 7,910,332 B2
(45) Date of Patent: Mar. 22, 2011

(54) METHOD FOR MANUFACTURING A RECOMBINANT POLYCLONAL PROTEIN

(75) Inventors: Lars Soegaard Nielsen, Nivaa (DK); Dietmar Weilguny, Virum (DK); Anne Bondgaard Tolstrup, Hillroed (DK); Finn C. Wiberg, Farum (DK); Christian Muller, Vaerlose (DK)

(73) Assignee: Symphogen A/S, Lyngby (DK)

( * ) Notice: Subject to any disclaimer, the term of this patent is extended or adjusted under 35 U.S.C. 154(b) by 103 days.

(21) Appl. No.: 12/153,809

(22) Filed: May 23, 2008

(65) Prior Publication Data

US 2009/0111142 A1 Apr. 30, 2009

Related U.S. Application Data

(60) Provisional application No. 60/960,002, filed on Sep. 11, 2007, provisional application No. 60/924,708, filed on May 29, 2007.

(30) Foreign Application Priority Data

May 25, 2007 (DK) ................................ 2007 00764
Sep. 7, 2007 (DK) ................................ 2007 01292

(51) Int. Cl.
*C12P 21/04* (2006.01)
*C12N 5/07* (2010.01)
*C12N 5/16* (2010.01)
*C07K 16/00* (2006.01)

(52) U.S. Cl. .................... 435/69.6; 435/326; 530/387.1; 530/389.1

(58) Field of Classification Search .................. None
See application file for complete search history.

(56) References Cited

U.S. PATENT DOCUMENTS

| 6,849,259 | B2 | 2/2005 | Haurum et al. | |
| 7,262,028 | B2 * | 8/2007 | Van Berkel et al. | ......... 435/69.6 |
| 2005/0170398 | A1 * | 8/2005 | Van Berkel et al. | ............... 435/6 |
| 2006/0275766 | A1 | 12/2006 | Haurum et al. | |
| 2007/0141048 | A1 | 6/2007 | Oleksiewicz et al. | |

FOREIGN PATENT DOCUMENTS

| EP | 1 293 564 A1 | 3/2003 |
| EP | 1 484 402 A2 | 12/2004 |
| WO | WO 91/16074 A1 | 10/1991 |
| WO | WO 98/37186 A1 | 8/1998 |
| WO | WO 2004/029284 A2 | 4/2004 |
| WO | WO 2004/061104 A2 | 7/2004 |
| WO | WO 2005/042774 A2 | 5/2005 |
| WO | WO 2006/007850 A1 | 1/2006 |
| WO | WO 2006/007853 A2 | 1/2006 |
| WO | WO 2007/065433 A2 | 6/2007 |
| WO | WO 2007/101441 A1 | 9/2007 |

OTHER PUBLICATIONS

Sautter and Enenkel. Selection of high-producing CHO cells using NPT selection marker with reduced enzyme activity. Biotechnology and Bioengineering, 2005. vol. 89, pp. 530-538.*

Boder, E.T. and Wittrup, K.D., "Yeast surface display for screening combinatorial polypeptides libraries," *Nat. Biotechnol.* 15:553-557, Nature Publishing Group (1997).
Bregenholt, S., et al., "Recombinant Human Polyclonal Antibodies: A New Class of Therapeutic Antibodies Against Viral Infections," *Curr. Pharm. Des.* 12:2007-2015, Bentham Science Publishers (Jan. 2006).
Brezinsky, S.C.G., et al., "A simple method for enriching populations of transfected CHO cells for cell of higher specific productivity," *J. Immunol. Meth.* 277:141-155, Elsevier Science (2003).
Canfield, S.M. and Morrison, S.L., "The Binding Affinity of Human IgG for its High Affinity Fc Receptor Is Determined by Multiple Amino Acids in the $C_H2$ Domain and Is Modulated by the Hinge Region," *J. Exp. Med.* 173:1483-1491, Rockefeller University Press (1991).
Cull, M.G., et al., "Screening for receptor ligands using large libraries of peptides linked to the C terminus of the *lac* repressor," *Proc. Natl. Acad. Sci. U.S.A.* 89:1865-1869, National Academy of Science (1992).
Czerinsky, C.C., et al., "A Solid-Phase Enzyme-Linked Immunospot (ELISPOT) Assay for Enumeration of Specific Antibody-Secreting Cells," *J. Immunol. Meth.* 65:109-121, Elsevier Science (1983).
Dreher, M.L., et al., "Colony assays for antibody fragments expressed in bacteria," *J. Immunol. Methods* 139:197-205, Elsevier Science (1991).
Fuchs, P., et al., "Targeting Recombinant Antibodies to the Surface of *Escherichia Coli*: Fusion to a Peptidoglycan Associated Lipoprotein," *Biotechnology* 9:1369-1372, Nature Publishing Group (1991).
Grabherr, R. and Ernst, W., "The Baculovirus Expression System as a Tool for Generating Diversity by Viral Surface Display," *Comb. Chem. High Throughput Screen.* 4:185-192, Bentham Science Publishers (2001).
Haurum, J. and Bregenholt, S., "Recombinant polyclonal antibodies: Therapeutic antibody technologies come full circle," *IDrugs* 8:404-409, Thomson Scientific (May 2005).
Haurum, J.S., "Recombinant polyclonal antibodies: the next generation of antibody therapeutics?," *Drug Discov. Today* 11 :655-660, Elsevier Science (Jul. 2006).
Huang, Y., et al., "An efficient and targeted gene integration system for high-level antibody expression," *J. Immunol. Methods* 322:28-39, Elsevier Science (Apr. 2007).
Kang, A.S., et al., "Linkage of recognition and replication functions by assembling combinatorial antibody Fab libraries along phage surfaces," *Proc. Natl. Acad. Sci.* 88:4363-4366, National Academy of Science (1991).

(Continued)

*Primary Examiner* — Anne M. Gussow
(74) *Attorney, Agent, or Firm* — Sterne, Kessler, Goldstein & Fox P.L.L.C.

(57) ABSTRACT

The invention relates to a method for manufacturing a recombinant polyclonal protein composition, in particular a recombinant polyclonal antibody composition. The method comprises obtaining a collection of cells transfected with a collection of variant nucleic acid sequences, wherein each cell in the collection is transfected with and capable of expressing one member of the collection, which encodes a distinct member of a polyclonal protein. The cells are cultured under suitable conditions for expression of the polyclonal protein, which is obtained from the cells or culture supernatant. The nucleic acid sequence is introduced into the cells by transfection with a collection of vectors. The present method is suitable for manufacturing recombinant polyclonal antibodies for therapeutic uses.

59 Claims, 11 Drawing Sheets

OTHER PUBLICATIONS

Kito, M., et aL, "Construction of engineered CHO strains for high-level production of recombinant proteins," *Appl. Microbiol. Biotechnol. 60*:442-448, Springer-Verlag (2002).

Kumpel, B.M., et al., "Section 1C: Assessment of the functional activities and IgG Fc receptor utilisation of 64 IgG Rh monoclonal antibodies," *Transfus. Clin. Biol. 9*:45-53, Elsevier Science (2002).

Logtenberg, T., "Antibody cocktails: next-generation biopharmaceuticals with improved potency," *Trends Biotechnol. 25*:390-394, Elsevier Science (Sep. 2007).

Meijer, P.-R., et al., "Isolation of Human Antibody Repertoires with Preservation of the Natural Heavy and Light Chain Pairing," *J. Mol. Biol. 358*:764-772, Elsevier Science (May 2006).

Poulsen, T.R., et al., "Kinetic, Affinity, and Diversity Limits of Human Polyclonal Antibody Responses against Tetanus Toxoid," *J. Immunol. 179*:3841-3850, The American Association of Immunologists (Sep. 2007).

Roberts, R.W. and Szostak, J.W., "RNA-peptide fusions for the in vitro selection of peptides and proteins," *Proc. Natl. Acad. Sci. 94*:12297-12302, National Academy of Sciences (1997).

Schaffitzel, C., et al., "Ribosome display: an in vitro method for selection and evolution of antibodies from libraries," *J. Immunol. Meth. 231*:119-135, Elsevier Science (1999).

Sharon, J., et al., "Recombinant Polyclonal Antibodies for Cancer Therapy," *J. Cell. Biochem. 96*:305-313, Wiley-Liss (2005).

Söderlind, E., et al., "Recombining germline-derived CDR sequences for creating diverse single-framework antibody libraries," *Nat. Biotechnol. 18*:852-856, Nature Publishing Group (2000).

Stirnadel, H.A., et al., "Genetic analysis of IgG subclass responses against RESA and MSP2 of Plasmodium falciparum in adults in Papua New Guinea," *Epidemiol.* Infect. 124:153-162, Cambridge University Press (2000).

Tolstrup, A.B., et al., "Development of recombinant human polyclonal antibodies for the treatment of complex human diseases," *Expert Opin. Biol. Ther. 6*:905-912, Ashley Publications (Sep. 2006).

Wiberg, F.C., et al., "Production of Target-Specific Recombinant Human Polyclonal Antibodies in Mammalian Cells," *Biotechnol. Bioeng. 94*:396-405, Wiley (Jun. 2006).

* cited by examiner

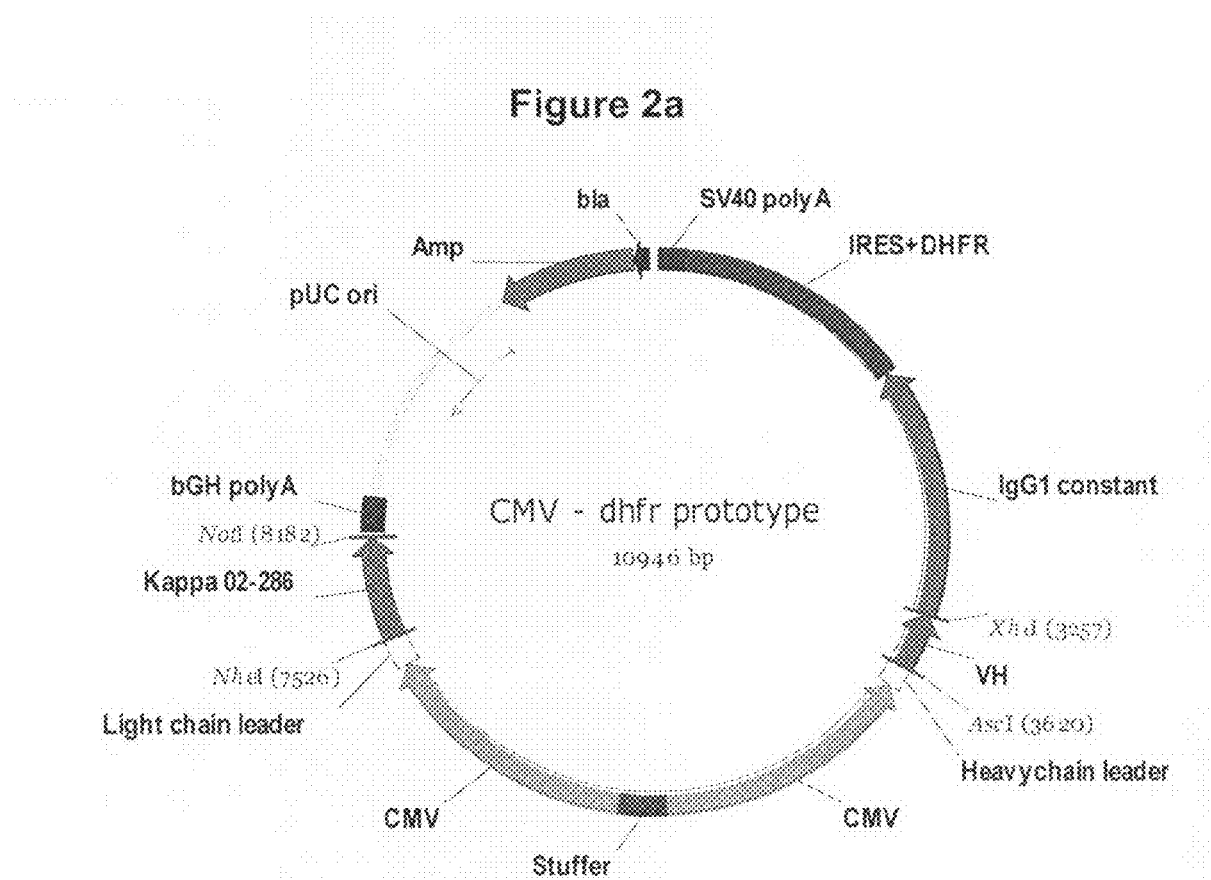
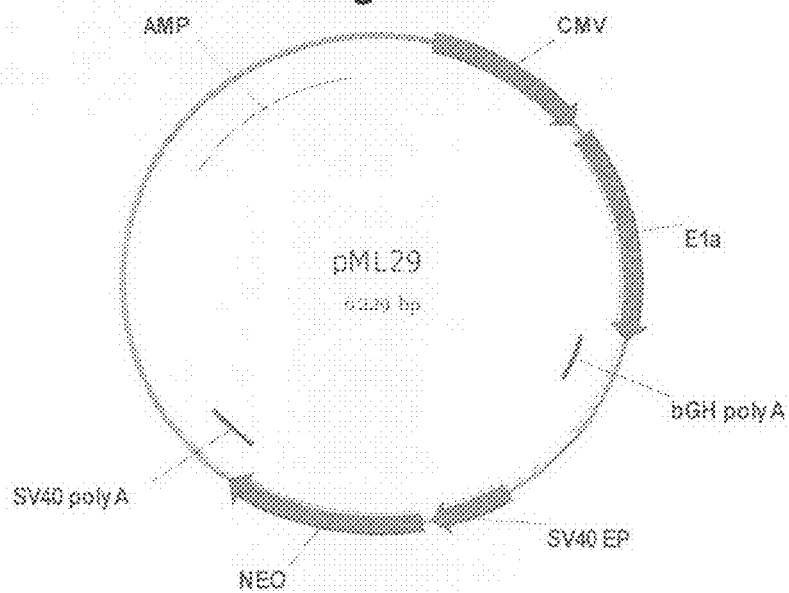

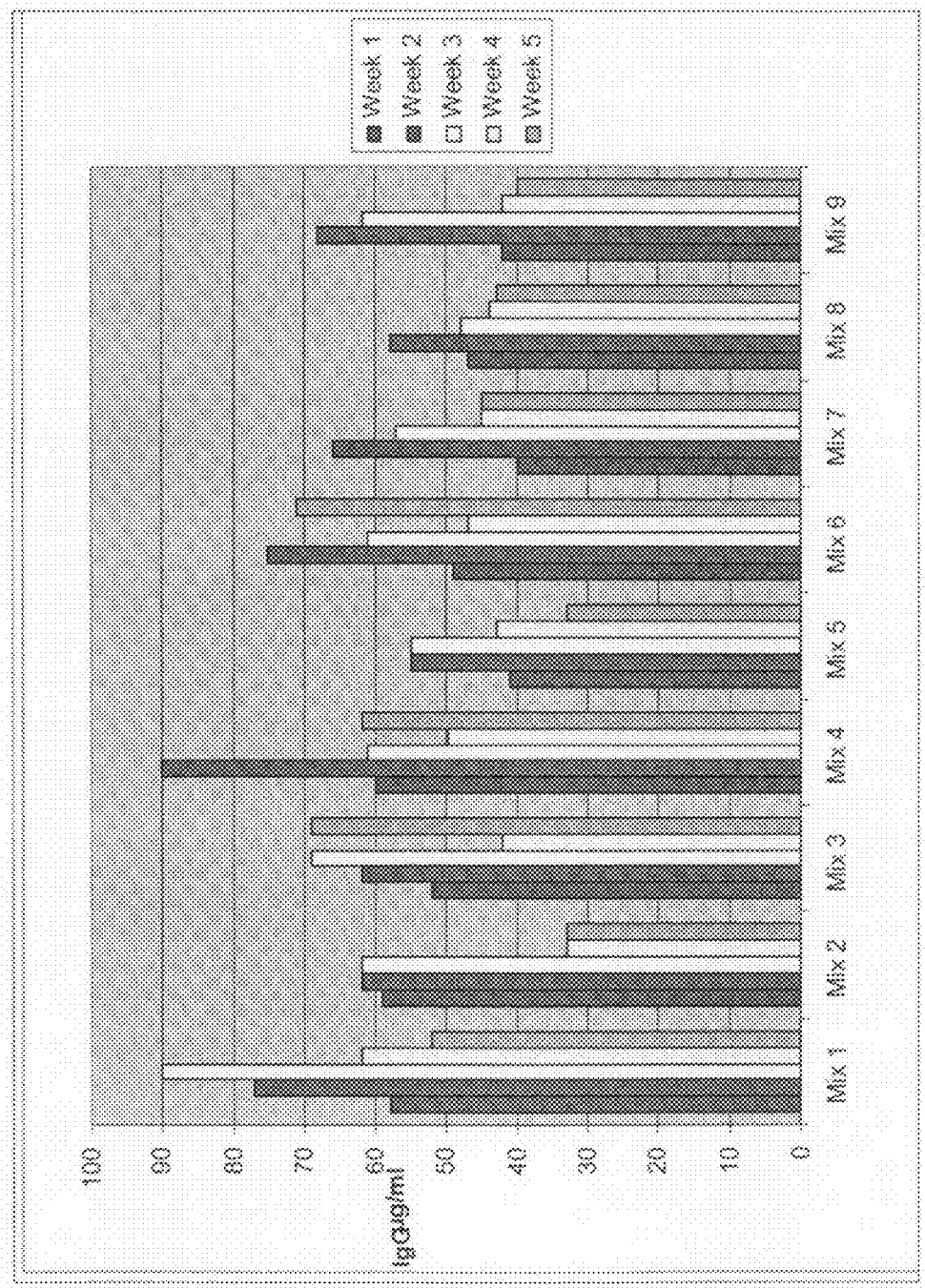

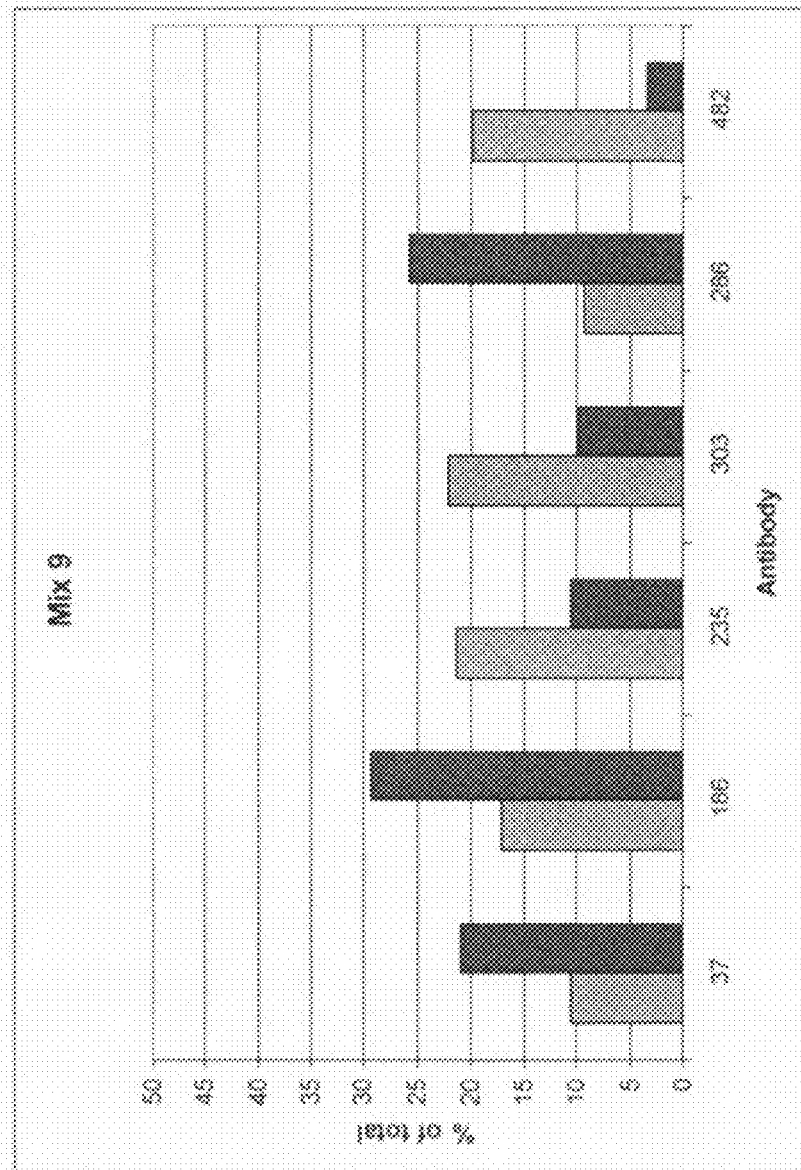

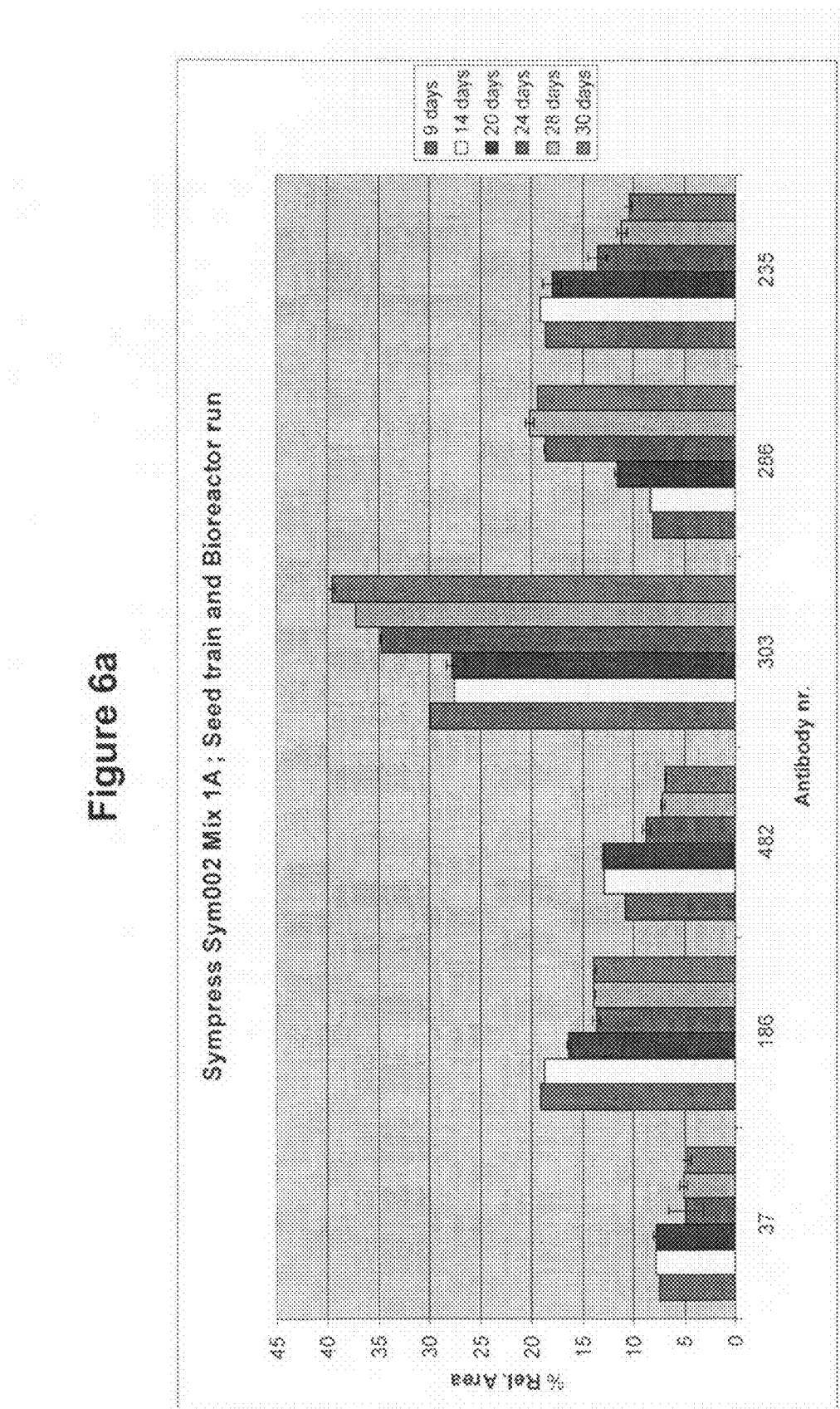

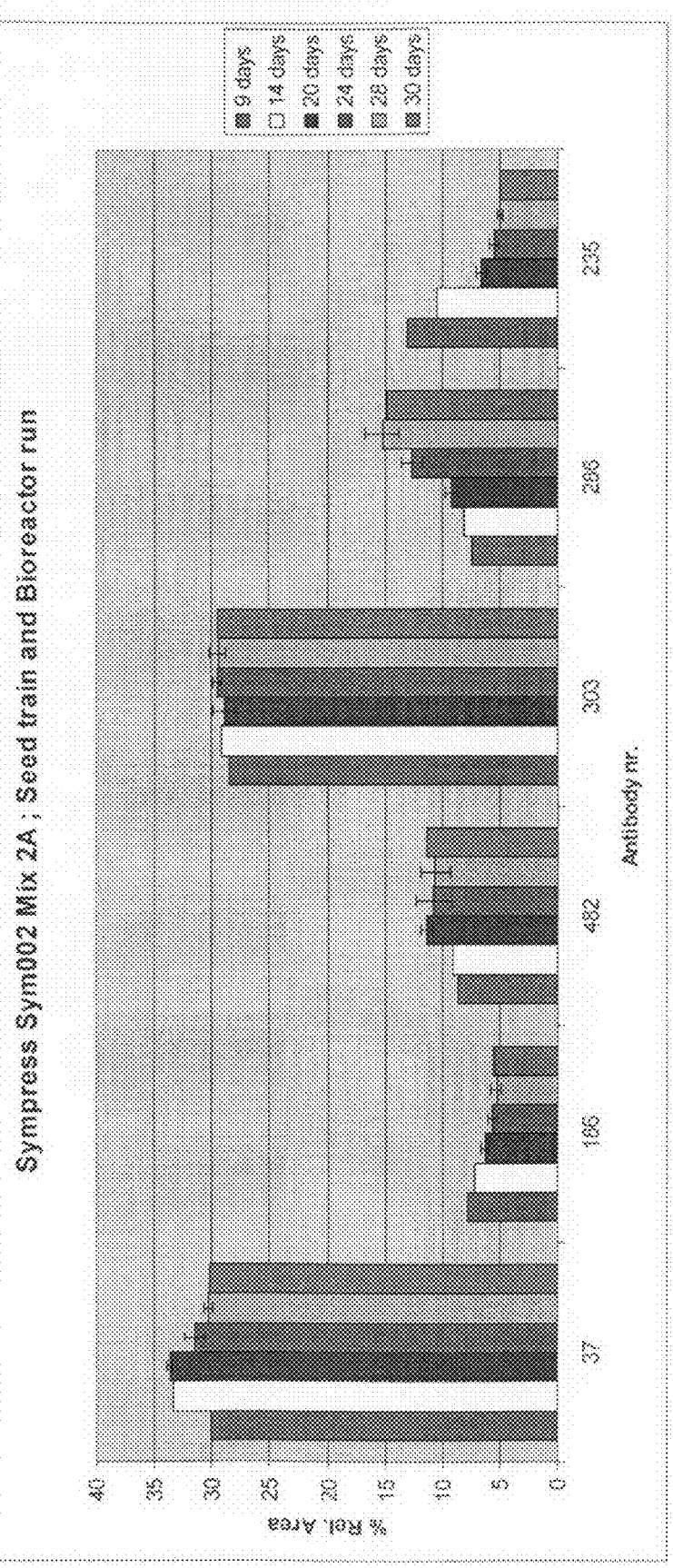

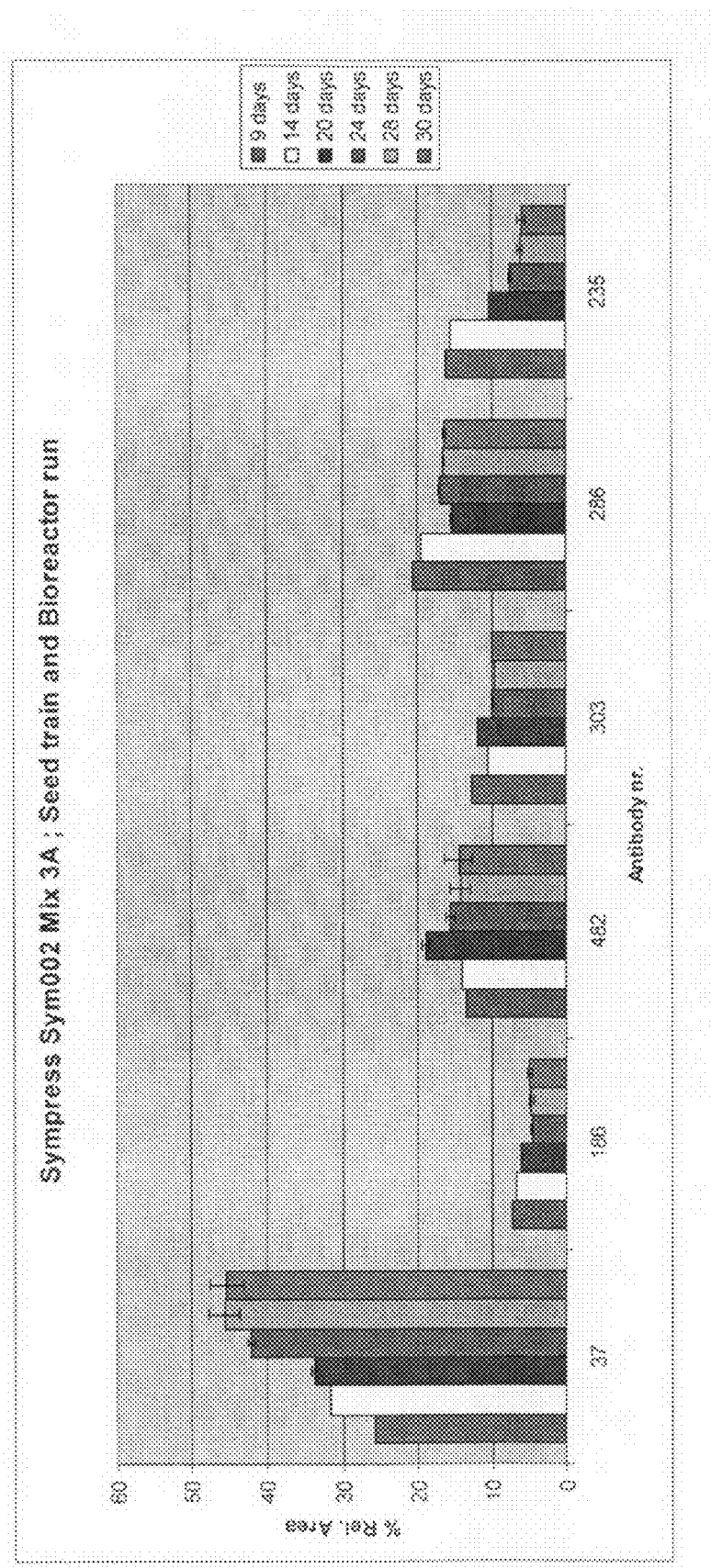

SEQUENCE LISTING

```
<160> NUMBER OF SEQ ID NOS: 3

<210> SEQ ID NO 1
<211> LENGTH: 870
<212> TYPE: DNA
<213> ORGANISM: adenovirus

<400> SEQUENCE: 1
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttttcc cgactctgta atgttggcgg tgcaggaagg gattgactta    240
ctcacttttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cggggaccc agatattatg tgttcgcttt gctatatgag gacctgtggc     540
atgtttgtct acagtcctgt gtctgaacct gagcctgagc ccgagccaga accggagcct     600
gcaagaccta cccgccgtcc taaaatggcg cctgctatcc tgagacgccc gacatcacct     660
gtgtctagag aatgcaatag tagtacggat agctgtgact ccggtccttc taacacacct     720
cctgagatac acccggtggt cccgctgtgc cccattaaac cagttgccgt gagagttggt     780
gggcgtcgcc aggctgtgga atgtatcgag gacttgctta acgagcctgg gcaacctttg     840
gacttgagct gtaaacgccc caggccataa                                      870
```

```
<210> SEQ ID NO 2
<211> LENGTH: 22
<212> TYPE: DNA
<213> ORGANISM: Artificial sequence
<220> FEATURE:
<223> OTHER INFORMATION: Synthetic PCR primer

<400> SEQUENCE: 2
tgactccggt ccttctaaca ca                                          22

<210> SEQ ID NO 3
<211> LENGTH: 21
<212> TYPE: DNA
<213> ORGANISM: Artificial sequence
<220> FEATURE:
<223> OTHER INFORMATION: Synthetic PCR primer

<400> SEQUENCE: 3
tcacggcaac tggtttaatg g                                           21
```

METHOD FOR MANUFACTURING A RECOMBINANT POLYCLONAL PROTEIN

This application claims the benefit of the filing date of U.S. Provisional Appl. No. 60/960,002, filed Sep. 11, 2007, U.S. Provisional Appl. No. 60/924,708, filed May 29, 2007, Danish Appl. No. PA 2007 00764, filed May 25, 2007, and Danish Appl. No. PA 2007 01292, filed Sep. 7, 2007, all of which are incorporated by reference in their entirety.

BACKGROUND OF THE INVENTION

1. Field of the Invention

The present invention relates to the production of recombinant polyclonal proteins, such as proteins from the immunoglobulin superfamily, e.g. soluble or membrane-bound forms of B or T cell receptors, using production systems which are independent of site-specific integration.

2. Background Art

A number of diseases such as infectious diseases and cancers lack efficient therapies. Monoclonal antibodies have generally not been successful against all of these targets, partly due to variability of the complex targets and adaptive mutations of target proteins causing immune escape from monoclonal antibody recognition. Polyclonal antibodies on the other hand are able to target a plurality of dynamic targets, e.g., on viruses, bacteria, or cancer cells. Also, polyclonal antibodies have the highest probability of retaining activity in the event of antigenic mutation.

Different commercially available polyclonal antibody therapeutics exist including: 1) normal human immunoglobulin isolated from the blood of normal human donors; 2) human hyperimmune immunoglobulin derived from the blood of individual human donors carrying antibodies against a particular disease target, e.g., a virus, which they previously have encountered either through infection or vaccination; and 3) animal hyperimmune immunoglobulin derived from the blood of immunized animals.

Immunoglobulin purified from human blood has proved effective against infections with hepatitis B virus, respiratory syncytial virus, cytomegalovirus and other herpes viruses, rabies virus, botulinum toxin, etc, as well as in the neonatal rhesus D prophylaxis. Immunoglobulin purified from the blood of rabbits immunized with human T cells is used to afford T cell immunosuppression in the treatment or prevention of transplant rejection (e.g., Thymoglobulin). Normal human immunoglobulin has been utilized to boost the immune system of immunodeficient patients, as well as in the therapy of various autoimmune disorders.

Nevertheless, widespread immunoglobulin use has been limited due to the constrained supply of donor blood raw material, problems with batch-to-batch variations, and variable safety. Animal-derived immunoglobulins in particular are faced with the same problems of immunogenicity as was observed for animal-derived monoclonal antibodies in the 1980s and 1990s. Finally, as with other blood products, the risk of transmission of infectious agents such as HIV, herpes or hepatitis viruses or prions remains. Accordingly, while clinicians acknowledge that polyclonal antibodies are a preferred therapeutic in some situations, their use has been very limited.

New approaches to generate human immunoglobulins arose with the transgenic animal techniques. Transgenic mice carrying human immunoglobulin loci have been created (U.S. Pat. No. 6,111,166). These mice produce fully human immunoglobulins, and antibodies against a specific target can be raised by usual immunization techniques. However, larger antibody yields are limited because of the relatively small size of mice. Larger animals have also been made transgenic for the human immunoglobulin genes, e.g., cows (Kuroiwa, Y. et al. *Nature Biotechnology;* 2002; 20: 889-893). However, producing polyclonal antibodies for therapy from the blood of such animals is not without complications. First, the immunophysiology of the animal and humans may display considerable differences, causing a difference in the resulting immune repertoire, functional rearrangement, and diversity of the antibody response. Second, mitotic instability of the introduced immunoglobulin loci might influence the long-term production of antibodies. Third, it is technically challenging to delete the animal's own immunoglobulin loci so that e.g., the animal antibody production will not exceed the production of human antibody. Fourth, the risk of transmission of infectious agents such as viruses, prions or other pathogens accompanies the administration of human antibodies produced in animals.

Recently, a new type of polyclonal antibodies which is independent on donor availability at the time of production has been developed. These polyclonal antibodies are generated by isolating antibody encoding nucleic acid sequences from donors with an immune response against the desired target, followed by screening for antibodies which specifically bind the desired target. The polyclonal antibody may be manufactured by an adapted mammalian expression technology, which is based on site-specific integration of one antibody expression plasmid into the same genomic site of each cell as described in WO 2004/061104. One example of this new type of polyclonal antibodies is a recombinant polyclonal antibody against Rhesus D (WO 2006/007850). The use of site-specific integration results in a cell population where each cell contains a single copy and where expression levels and growth rates are expected to be relatively uniform.

SUMMARY OF THE INVENTION

The present invention provides alternative methods for production of a recombinant polyclonal protein, which are independent of site-specific integration and therefore provide increased flexibility with respect to the choice of production cell line, while maintaining the polyclonality of the protein. In addition, expression levels may be higher than possible with site-specific integration.

The approach of the present invention is based on random integration of the individual genes of interest into host cells, preferably followed by cloning of single cells with desired characteristics. The individual cell clones, which each produce an individual member of the polyclonal protein, are then mixed in order to generate a polyclonal manufacturing cell line for the production of a polyclonal protein.

Polyclonal antibodies are generally the most well known polyclonal proteins. The same goes for T cell receptors (TcR's), which when produced in a recombinant expression system can be obtained in a soluble form which may have potential for treatment like the polyclonal antibodies. With the recombinant expression systems of the present invention it is however also possible to combine proteins which are not necessarily homologous, e.g. different proteins with known relevance in a particular deficiency or disease. The present invention will be exemplified by polyclonal antibodies, but it is intended to cover polyclonal TcR's and other polyclonal proteins which it may be desired to manufacture together. Such proteins may also be fusion proteins if desired.

The present invention allows for the commercial production of a recombinant polyclonal protein in one container, e.g. for use in pharmaceutical compositions. One important feature of the invention is that during the manufacturing process biased expression of the individual molecules constituting the polyclonal protein is kept to a low level, minimizing unwanted batch-to-batch variation and avoiding elimination of members of the polyclonal antibody during manufacture.

In one aspect the present invention relates to a method for generation of a polyclonal cell line capable of expressing a polyclonal protein comprising 2 to n distinct members, said method comprising:

a) Providing a set of expression vectors, wherein each of said vectors comprises at least one copy of a distinct nucleic acid encoding a distinct member of said polyclonal protein;

b) Separately transfecting host cells with each of said expression vectors under conditions avoiding site-specific integration of the expression vectors into the genome of the cells, thereby obtaining 2 to n compositions of cells, each composition expressing one distinct member of the polyclonal protein;

c) Mixing said 2 to n compositions of cells to obtain a polyclonal cell line.

In preferred embodiments the polyclonal cell line is used as a polyclonal manufacturing cell line and frozen and stored and used as a polyclonal Master Cell Bank (pMCB), from which samples (e.g. ampoules) can be thawed and used directly for manufacturing of recombinant polyclonal protein or generation of a polyclonal Working Cell Bank (pWCB).

In one embodiment the expression vectors are episomal vectors. In another, preferred embodiment, the expression vectors are stably and randomly integrated into the genome of the host cells. The expression vectors may be stably integrated at random positions in one or more chromosomes of a host cell.

Preferably the transfected cells obtained in step b) are cloned. In one embodiment cloning is performed using FACS cloning as described herein.

The clones may be selected for at least one criterion selected from the group consisting of: growth rate, doubling time, expression level, production level, stability of production over time, viability, hardiness, robustness, morphology, and copy number. Preferably, clones are selected for uniformity with respect to the at least one criterion. More preferably, clones are selected for uniformity with respect to doubling time and expression level.

One clone or more than one clone may be selected for each distinct polyclonal protein member. Thus, 2 clones may be selected for each distinct polyclonal protein member, or 3, 4, 5, 6, 7, 8, 9, 10, 11, 12, 13, 14, 15, 16, 17, 18, 19, 20, 25, 30, 35, 40, 45, 50, 60, 70, 80, 90, or 100 clones may be selected.

The compositions of cells expressing different distinct members may be mixed in a 1:1 ratio or in a ratio different from a 1:1 ratio. Preferably, the expression vectors are identical except for variations in the coding sequence of the polyclonal protein.

The method can be applied both to monomeric and multimeric polyclonal proteins.

In the case of multimeric proteins one expression vector may encode all subunits of one distinct polyclonal protein member. Alternatively the set of expression vectors in step a) is constituted of two or more sub-sets of expression vectors, where a first subset comprises variant nucleic acid sequences encoding one subunit of the protein, and a second subset comprises variant nucleic acid sequences encoding another subunit of the protein, such that each transfection is performed with a member from the first subset and a member for the second subset of expression vectors. This transfection may be simultaneous or sequential. Specifically, the set of expression vectors in step a) may be constituted of two subsets of expression vectors, where the first subset comprises variant nucleic acid sequences encoding an antibody heavy chain, and the second subset comprises variant nucleic acid sequences encoding an antibody light chain, such that each transfection is performed with a member from the first subset and a member for the second subset of expression vectors.

The expression vector or a further expression vector preferably encodes a selectable marker. Furthermore, cells are continuously cultured under conditions favouring growth of cells expressing the selectable marker. This is best ensured by using a selectable marker comprising a gene product, in which the host cell is deficient. The selectable marker in one embodiment is encoded by a transcript that also encodes a polypeptide member or a subunit of said polypeptide member, preferably wherein the selectable marker is encoded by the transcript encoding the largest subunit.

One aspect of the present invention relates to a method for manufacture of a polyclonal protein, wherein said polyclonal protein comprises 2-n distinct members, said method comprising:

a) providing a polyclonal cell line obtained using the method of the invention;

b) culturing the polyclonal cell line under conditions allowing for expression of the polyclonal protein; and c) recovering and optionally purifying the polyclonal protein from the cells or medium.

The present inventors have determined that surprisingly, the distribution of the individual clones is maintained during a simulation of a production cycle, which is representative of conditions for industrial manufacture of a recombinant drug product. This is very surprising, since the expression vectors for the individual members of the polyclonal antibody integrate at different positions and because the copy number differs. This could lead to differences in both expression level and growth rate.

Contrary to the expectation, the manufacturing did not result in the complete or partial loss of one or more members of the polyclonal antibody. Even with minor differences in growth rate among different cell lines, it is expected that a polyclonal composition over time will result in the complete or partial loss of at least one member of the polyclonal composition. Thus in embodiments of the invention the compositional stability is maintained during more than 10 cell divisions following thawing of the Working Cell Bank, preferably more than 15 cell divisions, such as more than 20 cell divisions, for example more than 25 cell divisions, such as more than 30 cell divisions, for example more than 40 cell divisions, such as more than 50 cell divisions, for example more than 75 cell divisions, such as more than 100 cell divisions.

The appended examples show that the compositional stability is maintained within acceptable limits during more than 25 cell divisions.

While separate transfection is preferred in the vast majority of cases, pooling of expression vectors prior to transfection is possible under certain conditions. If the polyclonal protein is a monomer this is indeed an option, as it is not a problem that one cell expresses several different members of the polyclonal protein. If the polyclonal protein is a multimer, pooling of expression vectors prior to transfection is only possible if means are used to ensure that only one copy is inserted into every cell. Otherwise undesired scrambling of the sub-units may occur.

While pooling of expression vectors is a definite possibility it is less preferred than separate transfection as it is expected to result in a less robust manufacturing system with respect to maintaining the compositional stability.

In both methods of the invention, it will be understood that the polyclonal protein normally is one that is not naturally associated with the cells wherein expression is effected.

The present invention describes several methods by which a library of variant nucleic acid sequences can be introduced into a host cell line in order to generate a collection of cells suitable as polyclonal manufacturing cell line. These methods include bulk transfection of a collection of cells with the library, semi-bulk transfection of aliquots of cells with fractions of the library or, preferably, individual transfection where host cells are transfected with individual members of the library followed by pooling of clones generated upon selection. Preferably the present invention utilizes mammalian cells (cell lines or cell types) as host cell line.

In one aspect of the invention, the individual members of a polyclonal protein are encoded from pairs of independent gene segments. Polyclonal proteins, where the individual members are comprised of two or more polypeptide chains, include soluble or membrane-bound forms of antibodies and T cell receptors. In further embodiments of the present invention a pair of gene segments encode an antibody heavy chain and light chain variable region, or a T cell receptor alpha chain and beta chain variable region or a T cell receptor gamma chain and delta chain variable region.

The present invention further provides a polyclonal cell line comprising 2 to n populations of cells each population expressing a distinct member of a recombinant polyclonal protein, the cells comprising at least one expression construct randomly integrated into the genome. In one embodiment the at least one expression construct is randomly integrated into an extra-chromosomal element. In another embodiment the at least one expression construct is integrated at random positions in one or more chromosomes of a host cell.

The cell line preferably originates from a mammalian cell line such as Chinese hamster ovary (CHO) cells, COS cells, BHK cells, myeloma cells (e.g., Sp2/0 cells, NS0, YB2/0), NIH 3T3, fibroblasts or immortalized human cells such as HeLa cells, HEK 293 cells, or PER.C6. However, non-mammalian eukaryotic or prokaryotic cells, such as plant cells, insect cells, yeast cells, bacteria, fingi etc., can also be used.

In a further aspect, the invention relates to a DHFR negative CHO cell comprising a stably integrated nucleic acid encoding an adenovirus type 5 transactivator E1A operably linked to a constitutive promoter.

Such a modified CHO cell line was constructed for the experiments leading to the other aspects of the invention. The cell line has turned out to be exceptionally stable with respect to uniformity of growth rates and expression levels and stability in these over time as is shown in the examples incorporated herein and is therefore especially adapted for use in the methods of the invention. Later experiments showed that E1A mRNA was not detectable in the twice sub-cloned cell. This means that the results showing a remarkable compositional stability cannot be ascribed solely to E1A expression. Still it is expected that a DHFR negative CHO cell line stably expressing E1A will result in a very stable and high expression cell line.

In a preferred embodiment the cell line is derived from a DG44 cell line, which is a homozygous DHFR knockout. This cell line can only survive in thymidine deficient medium if the cells comprise a recombinant DHFR expression construct.

In preferred embodiments, the cell line of the invention further comprises at least one copy of a stably integrated expressing construct coding for a polypeptide of interest. The polypeptide of interest may be a multimeric protein, preferably the multimeric protein is an antibody.

In order to allow for selection in thymidine deficient medium the expression construct coding for the polypeptide of interest further encodes dhfr.

Preferably dhfr and at least one subunit of the polypeptide of interest is encoded by the same transcript, more preferably dhfr is encoded by the transcript coding for the largest subunit. This leads to a strong linkage between the desired product, the polypeptide of interest, and the selection marker, dhfr, and ensures that surviving cells express the polypeptide of interest.

To further enhance expression of the polypeptide of interest, expression of the polypeptide of interest may be controlled by one or more promoters transactivatable by the transcriptional activator E1A, preferably wherein the promoter is a CMV promoter or derived from a CMV promoter.

DEFINITIONS

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

As used herein, the term "polyclonal protein" or "polyclonality" refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules or derivatives thereof (such as Fab Fab$_2$; single chain Fvs etc), T cell receptors and B cell receptors. A polyclonal protein may consist of a defined subset of protein molecules, which has been defined by a common feature such as the shared binding activity towards a desired target, e.g., in the case of a polyclonal antibody against the desired target antigen.

The term "polyclonal protein of interest" covers a defined polyclonal protein subset, which shares a common feature, such as binding activity towards a desired target, e.g., in the case of polyclonal antibodies described by the binding activity or specificity against the target antigen, said antigen being one or more of e.g., separate proteins, microorganisms, parasites, cell types, allergens, or carbohydrate molecules, or any other structures, molecules, or substances, which may be the target of specific antibody binding, or mixtures of said antigens.

The terms "one member of a recombinant polyclonal protein composition" or "one member of a recombinant polyclonal protein" denote one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The terms "variable polypeptide sequence" and "variable region" are used interchangeably.

The terms "a distinct member of a recombinant polyclonal protein" denotes one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or even on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein are also intended to include chimeric and single chain antibodies, as well as binding fragments of antibodies, such as Fab, Fv fragments or scFv fragments, as well as multimeric forms such as dimeric IgA molecules or pentavalent IgM.

The term "polyclonal antibody" describes a composition of different antibody molecules which is capable of binding to or reacting with several different specific antigenic determinants on the same or on different antigens. Usually, the variability of a polyclonal antibody is thought to be located in the so-called variable regions of the polyclonal antibody. However, in the context of the present invention, polyclonality can also be understood to describe differences between the individual antibody molecules residing in so-called constant regions, e.g., as in the case of mixtures of antibodies containing two or more antibody isotypes such as the human isotypes IgG1, IgG2, IgG3, IgG4, IgA1, IgA2, IgM, IgD, and IgE, or the murine isotypes IgG1, IgG2a, IgG2b, IgG3, and IgA.

A "recombinant polyclonal antibody of interest" describes a defined recombinant polyclonal antibody subset, which is characterized by the ability to bind to a desired target or desired set of targets, said targets being e.g., a separate protein, a microorganism, a parasite, a cell, an allergen, or a carbohydrate molecule, or another structure, molecule, or substance which may be the target of specific antibody binding, or mixtures thereof.

The term "immunoglobulin" commonly is used as a collective designation of the mixture of antibodies found in blood or serum, but may also be used to designate a mixture of antibodies derived from other sources.

The term "immunoglobulin molecule" denotes an individual antibody molecule, e.g., as being a part of immunoglobulin, or part of any polyclonal or monoclonal antibody composition.

When stating that a member of a polyclonal protein binds to an antigen, it is herein meant a binding having binding constant that is below 1 mM, preferably below 100 nM, even more preferred below 10 nM.

The term "a library of variant nucleic acid molecules of interest" is used to describe the collection of nucleic acid molecules, which collectively encode a "recombinant polyclonal protein of interest". When used for transfection, the library of variant nucleic acid molecules of interest is contained in a library of expression vectors. Such a library typically have at least 2, 3, 4, 5, 6, 10, 20, 50, 1000, $10^4$, $10^5$ or $10^6$ distinct members.

As used herein the term "distinct nucleic acid sequence" is to be understood as a nucleic acid sequence which may encode different polypeptide chains that together constitute the protein of interest. Where the distinct nucleic acid sequence is comprised of more than one encoding sequence, these sequences may be in the form of a dicistronic transcription unit or they may be operated as two separate transcriptional units if operably linked to suitable promoters. Likewise the use of tri- and quattrocistronic transcription units is conceivable if the protein of interest consists of 3 or 4 sub-units, or if a selection marker is included into a transcriptional unit together with a nucleic acid coding for a protein of interest or a sub-unit thereof. Preferably, a distinct nucleic acid sequence of the present invention is part of a nucleic acid molecule such as e.g. a vector. Some examples, where more than one encoding sequence is required to give rise to a complete molecule of a protein of interest, include B cell receptors, antibodies and fragments of antibodies such as Fab's and variable domains, or T cell receptors. When introduced into the cell, the genes, which together encode the fully assembled protein of interest, reside in the same vector, thus being linked together in one nucleic acid sequence.

The term "a gene of interest" as used herein, refer to a nucleic acid sequence composed of one or more gene segments (genomic or cDNA) that encode one member of a protein of interest. The plural form "genes of interest" refers to a library of nucleic acid sequences encoding a polyclonal protein of interest. The term "GOI" is used as an abbreviation of (a) gene(s) of interest.

As used herein, the term "vector" refers to a nucleic acid molecule into which a nucleic acid sequence can be inserted for transport between different genetic environments and/or for expression in a host cell. If the vector carries regulatory elements for transcription of the nucleic acid sequence inserted in the vector (at least a suitable promoter), the vector is herein called "an expression vector". If the nucleic acid sequence inserted into the above identified vectors encodes a protein of interest as herein defined, the following terms are used "vector of interest" and "expression vector of interest". The term "an isotype-encoding vector" refers to a vector carrying nucleic acid sequences encoding an antibody isotype. In the present specification, "phagemid vector" and "phage vector" are used interchangeably. The terms "plasmid" and "vector" are used interchangeably. The invention is intended to include such other forms of vectors, which serve equivalent functions for example plasmids, phagemids and virus genomes or any nucleic acid molecules capable of directing the production of a desired protein in a proper host.

The term "each member of the library of vectors of interest" is used to describe individual vector molecules with a distinct nucleic acid sequence derived from a library of vectors of interest, where the nucleic acid sequence encodes for one member of the recombinant polyclonal protein of interest.

The term "mass transfer" is used to describe the transfer of nucleic acid sequences of interest from one population of vectors to another population of vectors and doing so for each DNA simultaneously without resorting to isolation of the individual DNA's of interest. Such populations of vectors can be libraries containing for example variable regions, promoters, leaders or enhancing elements of interest. These sequences can then be moved without prior isolation from for example a phage vector to a mammalian expression vector. Especially for antibody sequences this technique ensures that the linkage between $V_H$ and $V_L$ diversity is not lost while moving libraries from, for example, a selection vector (e.g., a phage display vector) to a mammalian expression vector. Hereby the original pairing of $V_H$ and $V_L$ is retained.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The term "selection" is used to describe a method where cells have acquired a certain characteristic that enable the isolation from cells that have not acquired that characteristic. Such characteristics can be resistance to a cytotoxic agent or production of an essential nutrient, enzyme, or color.

The terms "selectable marker gene", "selection marker gene", "selection gene" and "marker gene" are used to describe a gene encoding a selectable marker (e.g., a gene conferring resistance against some cytotoxic drug such as certain antibiotics, a gene capable of producing an essential nutrient which can be depleted from the growth medium, a gene encoding an enzyme producing analyzable metabolites or a gene encoding a colored protein which for example can be sorted by FACS) which is co-introduced into the cells together with the gene(s) of interest.

The term "recombinant protein" is used to describe a protein that is expressed from a cell line transfected with an expression vector comprising the coding sequence of the protein.

As used herein, the term "operably linked" refers to a segment being linked to another segment when placed into a functional relationship with the other segment. For example, DNA encoding a signal sequence is operably linked to DNA encoding a polypeptide if it is expressed as a leader that participates in the transfer of the polypeptide to the endoplasmic reticulum. Also, a promoter or enhancer is operably linked to a coding sequence if it stimulates the transcription of the sequence.

The term "a majority of the individual cells" refers to a percentage of the cells such as more than 80%, preferably more than 85%, more preferably 90%, 95%, or even 99% or higher.

As used herein, the term "genome" is not to be taken literally as the normal complement of chromosomes present in a cell, but also extra-chromosomal elements that can be introduced into and maintained in a cell. Such extra-chromosomal elements can include, but are not limited to, minichromosomes, YACs (yeast artificial chromosomes), MACs (mouse artificial chromosomes), or HACs (human artificial chromosomes).

The term "promoter" refers to a region of DNA involved in binding the RNA polymerase to initiate transcription.

The term "head-to-head promoters" refers to a promoter pair being placed in close proximity so that transcription of two gene fragments driven by the promoters occurs in opposite directions. A head-to-head promoter can also be constructed with a stuffer composed of irrelevant nucleic acids between the two promoters. Such a stuffer fragment can easily contain more than 500 nucleotides.

An "antibiotic resistance gene" is a gene encoding a protein that can overcome the inhibitory or toxic effect that an antibiotic has on a cell ensuring the survival and continued proliferation of cells in the presence of the antibiotic.

The term "internal ribosome entry site" or "IRES" describes a structure different from the normal 5' cap-structure on an mRNA. Both structures can be recognized by a ribosome to initiate scanning for an AUG codon to initiate translation. By using one promoter sequence and two initiating AUG's, a first and a second polypeptide sequence can be translated from a single mRNA. Thus, to enable co-translation of a first and a second polynucleotide sequence from a single bi-cistronic mRNA, the first and second polynucleotide sequence can be transcriptionally fused via a linker sequence including an IRES sequence that enables translation of the polynucleotide sequence downstream of the IRES sequence. In this case, a transcribed bi-cistronic RNA molecule will be translated from both the capped 5' end and from the internal IRES sequence of the bi-cistronic RNA molecule to thereby produce both the first and the second polypeptide.

The term "inducible expression" is used to describe expression that requires interaction of an inducer molecule or the release of a co-repressor molecule and a regulatory protein for expression to take place.

The term "constitutive expression" refers to expression which is not usually inducible.

The term "scrambling" describes situations where two or more distinct members of a polyclonal protein each comprised of two or more different polypeptide chains, e.g. from the immunoglobulin superfamily, is expressed from an individual cell. This situation may arise when the individual cell has integrated, into the genome, more than one pair of gene segments, where each pair of gene segments encode a distinct member of the polyclonal protein. In such situations unintended combinations of the polypeptide chains expressed from the gene segments can be made. These unintended combinations of polypeptide chains might not have any therapeutic effect.

The term "$V_H$-$V_L$ chain scrambling" is an example of the scrambling defined above. In this example the $V_H$ and $V_L$ encoding gene segments constitute a pair of gene segments. The scrambling occurs when unintended combinations of $V_H$ and $V_L$ polypeptides are produced from a cell where two different $V_H$ and $V_L$ encoding gene segment pairs are integrated into the same cell. Such a scrambled antibody molecule is not likely to retain the original specificity, and thus might not have any therapeutic effect or even an unintended therapeutic effect.

The term "recombinant polyclonal manufacturing cell line" refers to a population of protein expressing cells that are transfected with a library of variant nucleic acid sequences of interest such that the individual cells, which together constitute the recombinant polyclonal manufacturing cell line, carry one or more copies of a distinct nucleic acid sequence of interest, which encodes one member of the recombinant polyclonal protein of interest, and that each copy is integrated into the genome of each cell. The cells constituting the recombinant polyclonal manufacturing cell line are selected for their ability to retain the integrated copy of the distinct nucleic acid sequence of interest, for example by antibiotic selection. Cells which can constitute such a manufacturing cell line can be for example bacteria, fungi, eukaryotic cells, such as yeast, insect cells or mammalian cells, especially immortal mammalian cell lines such as CHO cells, COS cells, BHK cells, myeloma cells (e.g., Sp2/0 cells, NS0, YB2/0), NIH 3T3, and immortalized human cells, such as HeLa cells, HEK 293 cells, or PER.C6.

The term "bias" is used to denote the phenomenon during recombinant polyclonal protein production, wherein the composition of a polyclonal vector, polyclonal cell line, or polyclonal protein alters over time due to random genetic mutations, differences in proliferation kinetics between individual cells, differences in expression levels between different expression construct sequences, or differences in the cloning efficiency of DNA.

The term "RFLP" refers to "restriction fragment length polymorphism", a method whereby the migratory gel pattern of nucleic acid molecule fragments is analyzed after cleavage with restriction enzymes.

The term "5'UTR" refers to a 5' untranslated region of the mRNA.

The term "conditions avoiding site specific integration" refers to a transfection process which does not include any of the possible ways to obtain site specific integration. Site specific integration can e.g. be achieved using a combination of a recombinase and a recognition site for the recombinase in a chromosome of the host cell. The recombinase may also be covalently linked to a nucleotide stretch recognising a particular site in a chromosome. Site-specific integration can also be achieved—albeit at a lower efficiency—using homologous recombination. Avoiding site-specific integration will often result in integration at random positions throughout the genome of the host cell, if integration vectors are used.

The term "random integration" refers to integration of an expression vector into the genome of a host cell at positions that are random. The dictionary meaning of random is that there are equal chances for each item, in this case integration site. When transfecting cells all integration sites do not represent absolutely equal chances of integration as some parts of the chromosomes are more prone to integration events than others. When nothing is done to guide the expression vector to a particular integration site, it will integrate at positions that are random within the group of possible integration sites. Therefore, "random integration" in the context of the present invention is to be understood as a transfection procedure where nothing is done to guide the expression construct to a predetermined position. The absence of means to guide the expression vector to a predetermined position suffices to ensure "random integration". Thereby integration site(s) will vary from cell to cell in a transfected population, and the exact integration site(s) can be regarded unpredictable.

The term "stably integrated" refers to integration of an expression vector into the genome of a host cell, wherein the integration remains stable over at least 20, more preferably 30, more preferably 40, more preferably 50, such as 75, for example 100 generations or more.

Abbreviations: "CMV"=(human) Cytomegalo Virus. "AdMLP"=Adenovirus Major Late Promoter. SV40 poly A=Simian Virus 40 poly A signal sequence. GFP=Green Flourescent Proteins. TcR=T cell receptor. ELISA=Enzyme-Linked Immunosorbent Assay. LTR=Long Terminal Repeat.

The figure schematically illustrates the steps required to obtain a polyclonal cell bank, e.g. a polyclonal master cell bank. a) illustrates different expression vectors $N.A._1$, $N.A._2$, $N.A._3$, etc each encoding a different and distinct member of the polyclonal protein. b) illustrates the host cells to be transfected with the expression vectors. c) illustrates integration of the expression vectors at different positions and in different copy numbers in individual cells. d) illustrates selection of cellular clones for each of the members of the polyclonal protein. In this particular case, for ease of illustration, only one clone per distinct member of the polyclonal protein is shown. Step e) illustrates mixing of the clones selected in step d) to generate a polyclonal cell bank.

FIG. 2a. Prototype vector encoding heavy and light chain
The elements are as follows:
two identical head-to-head human CMV promoters with a spacer element in between
coding regions for heavy (VH+gamma 1 constant region) and light chain (kappa 02-286)
bGH=bovine growth hormone polyadenylation sequence
SV40 pA=SV40 polyadenylation sequence
Genomic leaders for heavy and light chain
IRES+DHFR=ECMV internal ribosome entry site and the mouse dihydrofolate reductase cDNA
pUC ori=pUC origin of replication
bla, amp=ampicilline resistance gene FIG. 2b. E1A expression vector pML29
The elements are as follows:
The vector is based on pcDNA3.1+(Invitrogen)
CMV=human CMV promoter
E1a=cDNA for adenovirus type 5 13S transactivator
bGH=bovine growth hormone polyadenylation region
SV40EP=SV40 early promoter
Neo=the neo resistance gene
SV40 polyA=SV40 polyadenylation region
AMP=β-lactamase gene encoding ampicillin resistance FIG. 3. IgG content of mixes 1-9 during the 5 week period the experiment was performed. For detail, see Example 1.

Figure 4:
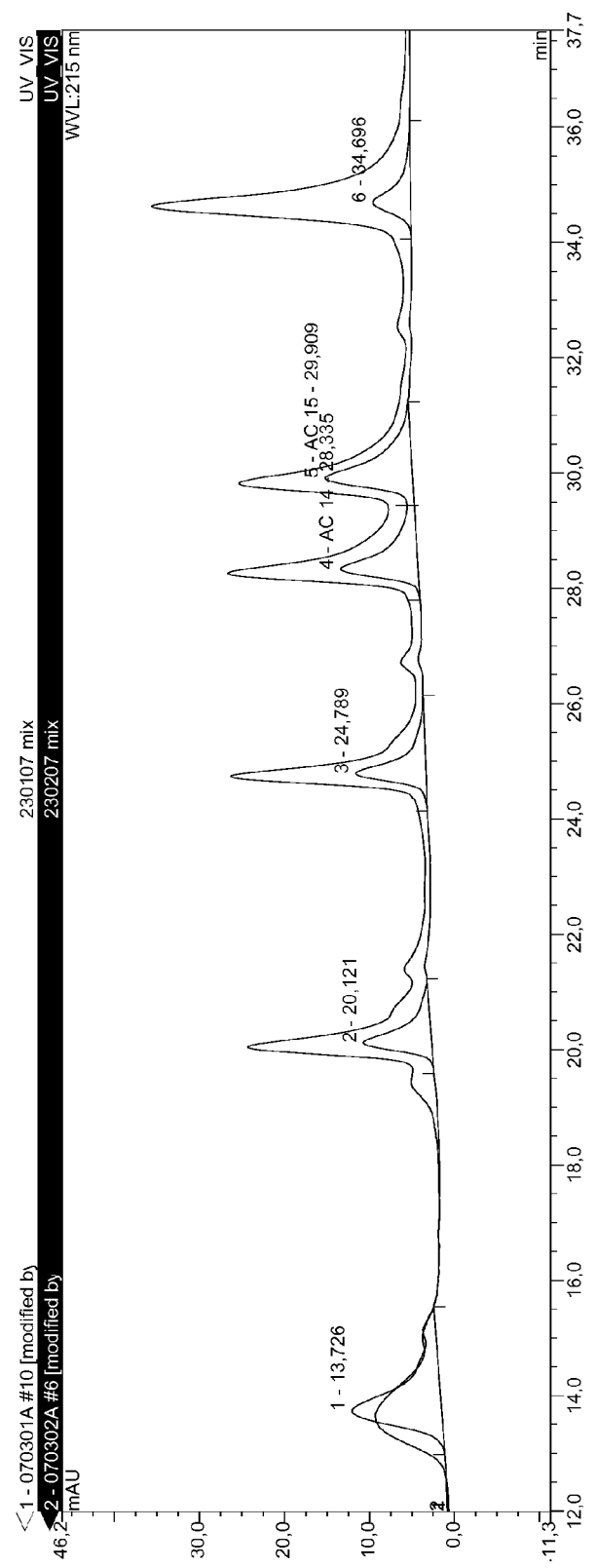

FIG. 4. Ion exchange chromatograms showing the composition of Mix 8 at start and end of the 5 week culture period.

Figure 5A:
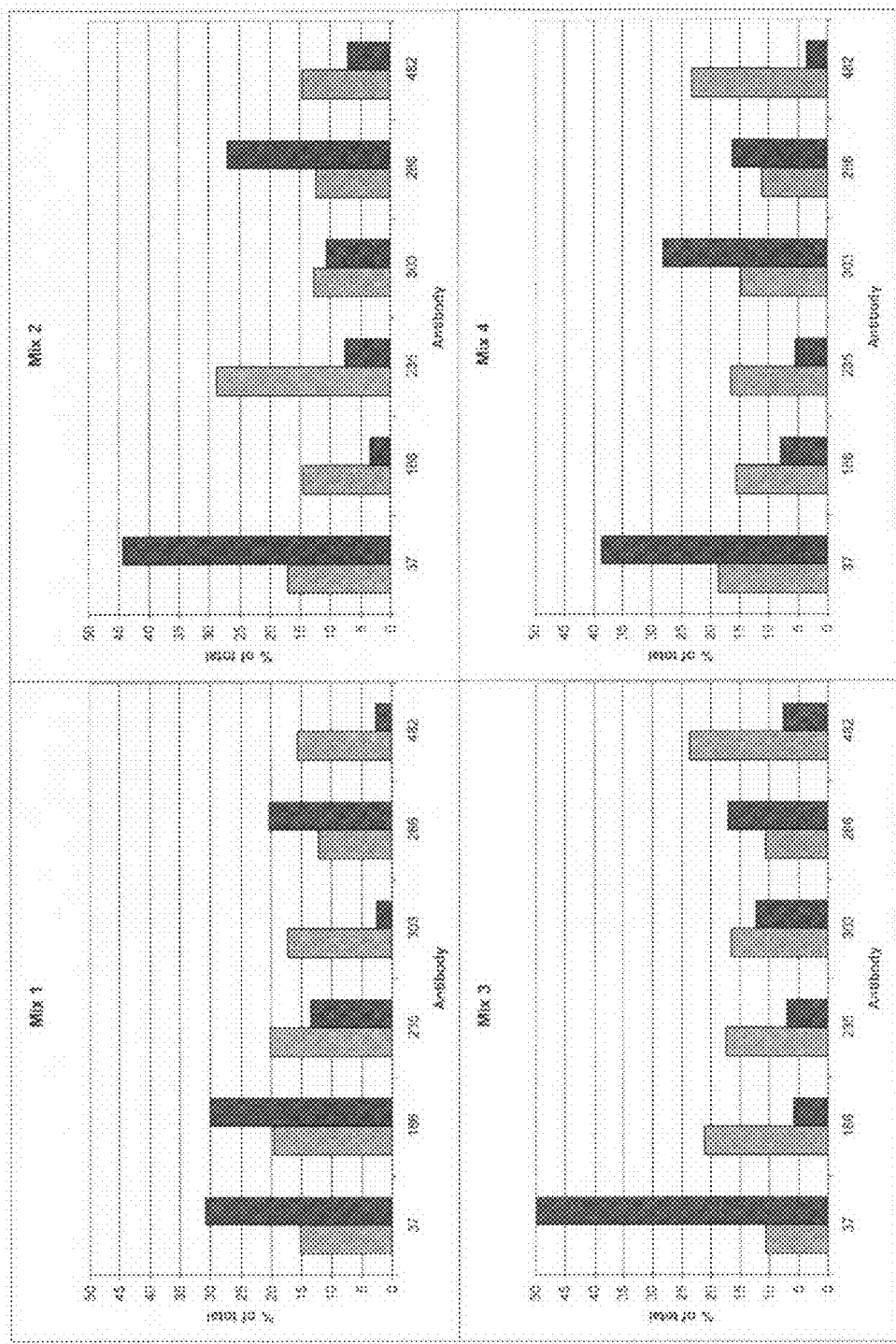
Figure 5B:
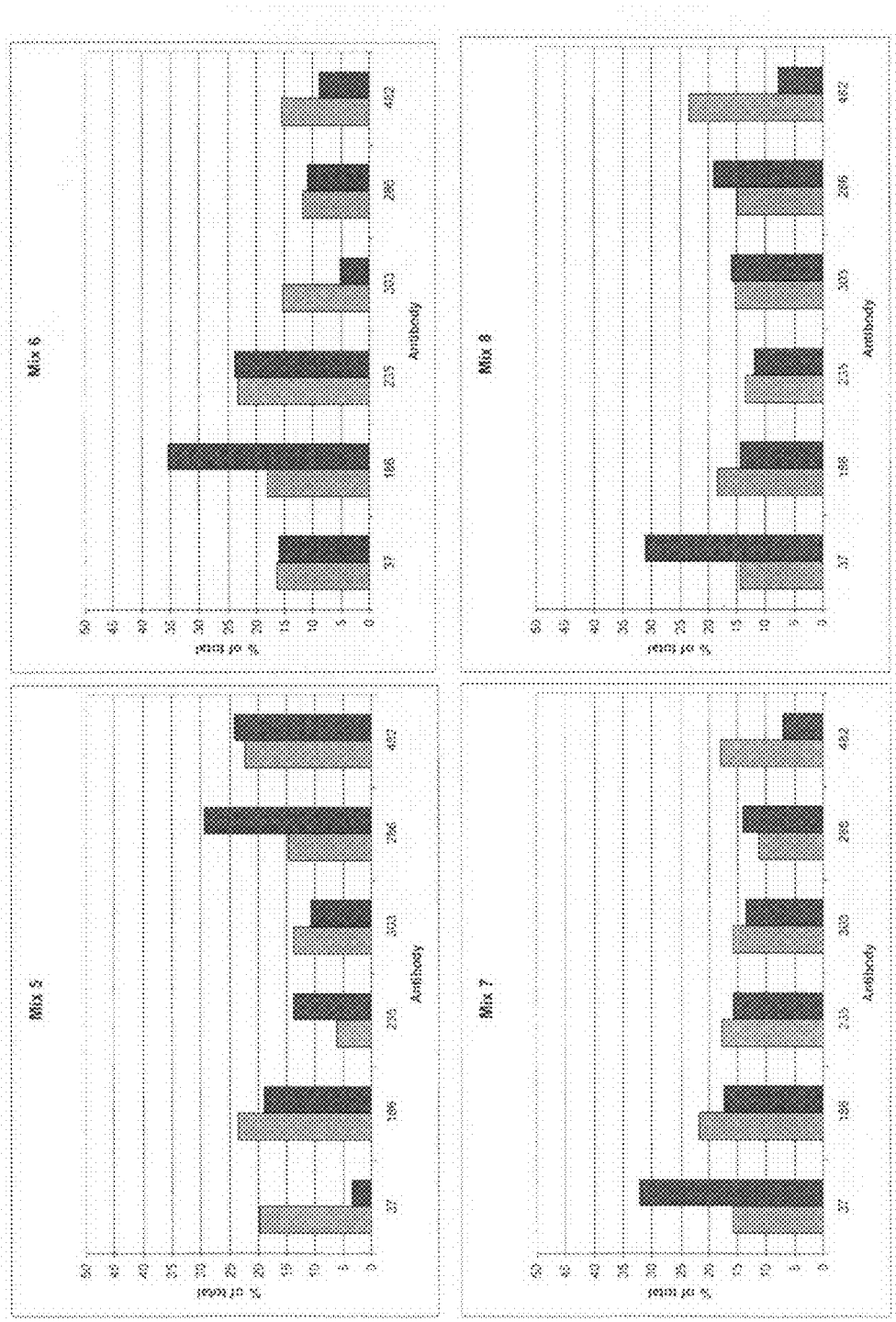

FIG. 5a-c. First (grey) and last (black) sample from all 9 mixes were analyzed by ion exchange chromatography and the content of each individual antibody was calculated and shown graphically.

Figure 6D:
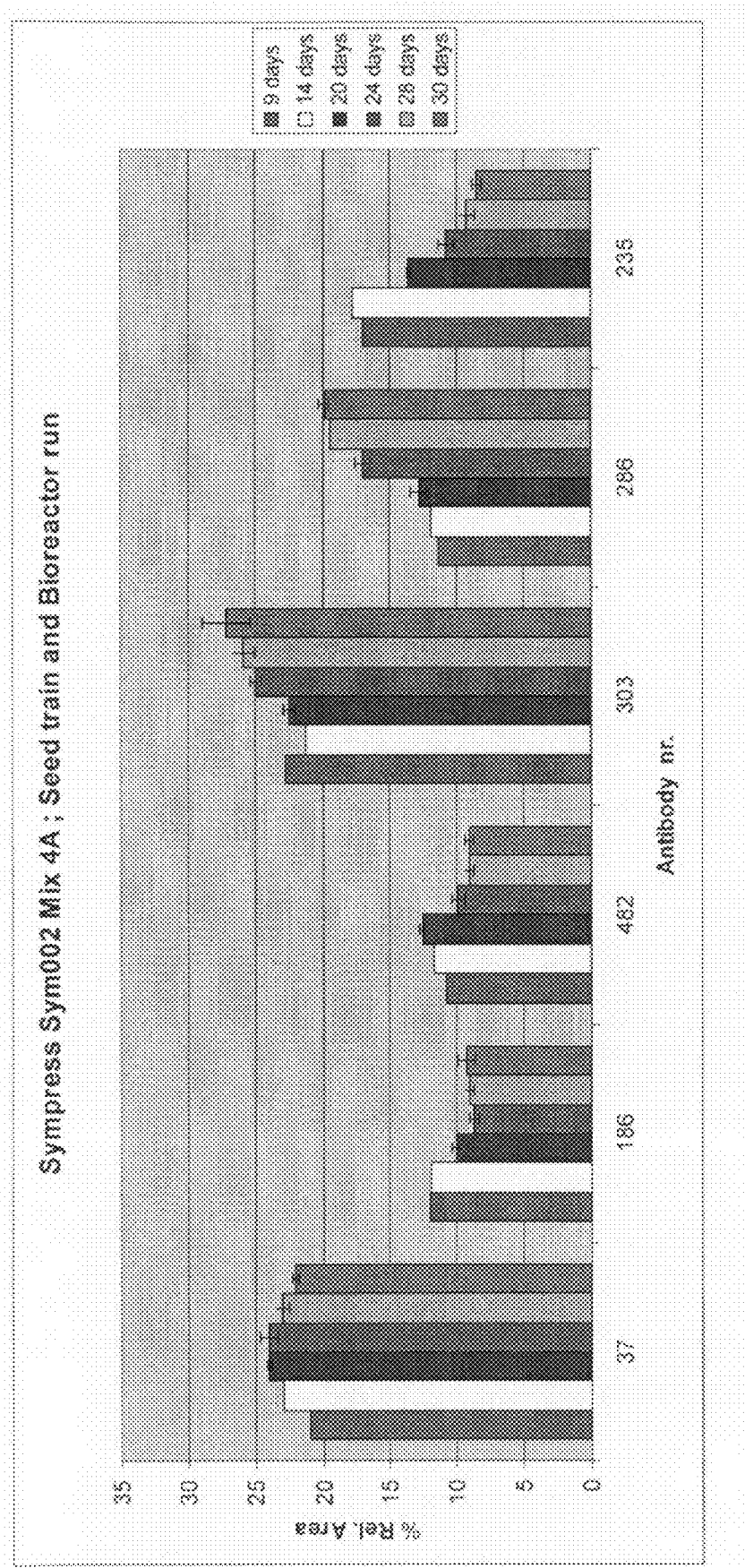

FIG. 6. Samples from the 4 mixes (Example 5) during seed train and bioreactor run were analyzed by ion exchange chromatography and the content of each individual antibody was calculated and shown graphically.

Mix 1 A-3 A contained a single clone per antibody. The cell clones expressing each of the 6 antibodies were different in mix 1 A (FIG. 6a), mix 2 A (FIG. 6b) and mix 3 A (FIG. 6c).

Mix 4 A (FIG. 6d) contained 3 clones per antibody.

DETAILED DESCRIPTION OF THE INVENTION

The Recombinant Polyclonal Protein Expression System

The present invention provides methods for the consistent manufacturing of recombinant polyclonal proteins that are preferably selected from the immunoglobulin superfamily, a family of proteins with immunoglobulin-like domains. Most of the members are involved in cell surface recognition events. Sequence analysis suggests that antibodies, T cell receptors, MHC molecules, some cell adhesion molecules and cytokines receptors are highly homologous. Especially members of this family that contain variable regions are suitable for the generation of recombinant polyclonal proteins according to the present invention. Such members include antibodies, membrane bound antibodies (B cell receptors), Fab fragments, Fv fragments, single chain Fv (scFv) fragments, T cell Receptors (TcRs), soluble TcRs, TcR variable domain fragments, TcR variable domain fragments linked by a polypeptide linker or other antibody or TcR derived fragments. In particular, it is contemplated that the present invention can be used for large-scale manufacturing and production of recombinant therapeutic polyclonal antibodies and TcRs.

One of the major advantages of the manufacturing method of the present invention is that all the members constituting the recombinant polyclonal protein can be produced in one or a few bioreactors or equivalents thereof. Further, the recombinant polyclonal protein composition can be purified from the reactor as a single preparation without having to separate the individual members constituting the recombinant polyclonal protein during the process. In contrast, if one wanted to mimic a recombinant polyclonal antibody composition by mixing purified monoclonal antibodies (as for example proposed in WO 91/16074) it would require the separate manufacturing in a bioreactor of each antibody to be included in the composition and the antibodies would be purified individually as well. Such a production of a monoclonal mixture would be very costly, and time and space consuming compared to the method of producing recombinant polyclonal antibody or other polyclonal proteins as described herein. Thus, the method as described in WO 91/16074 would naturally result in a practical limit to the number of monoclonal antibodies that could be included in such a mixture, whereas the technology as described herein generally can produce a polyclonal antibody with many individual members, in principle without an upper limit.

The host cell line used is preferably a mammalian cell line comprising those typically used for biopharmaceutical protein expression, e.g., CHO cells, COS cells, BHK cells, myeloma cells (e.g., Sp2/0 cells, NS0, YB2/0), NIH 3T3, and immortalized human cells, such as HeLa cells, HEK 293 cells, or PER.C6. In the present invention CHO cells were used, more particularly a modified DG44 clone. The choice of this particular cell line has been made because CHO cells are widely used for recombinant manufacture of antibodies and because the DG44 clone can be used in combination with the metabolic selection marker DHFR, which additionally allows for amplification of the encoded gene.

The DG44 cell line has been modified by transfection with a E1A transactivator encoding expression vector. This has been done to increase the overall yield, when the gene of interest is operatively linked to a CMV promoter. The CMV promoter is transactivated by E1A. The modification has provided an exceptionally stable cell line providing cell clones having uniform growth rates and uniform and high expression levels for different antibodies. The modification is therefore believed to improve compositional stability over time. Attempts to detect E1A expression in the modified cell line have failed. It is therefore not likely that the uniform growth rates and uniform and high expression levels can be ascribed solely to E1A expression. While in the present case E1A expression was undetectable, it is still believed that transactivation of the CMV promoter using E1A expression could lead to even higher and stable expression levels.

BHK-21 cells or CHO cells are preferably used for expression. Suitable CHO cells include but are not limited to CHO-K1 and CHO-S cells. Dhfr-minus mutants of CHO such as CHO-DUKX-B11 or DG44, are preferred mammalian cells for the practice of this invention. These cells are well known in the art and widely available, for example, from the American Type Culture Collection, (A.T.C.C.) Rockville, Md. (BHK-21) or from Dr. Lawrence Chasin, Columbia University, New York (CHO DUKX-B11 or DG44). These cells adapt well to growth in suspension cultures (also under serum-free conditions) and/or can grow under low serum concentrations and can be used in conjunction with the DHFR selection marker.

The cell line is preferably subcloned and selected for clones showing a high and stable expression of member(s) of the polyclonal protein.

Consequently, a person of ordinary skill in the art would be able to substitute the DG44 clone with other clones and substitute CHO cells with other mammalian cells as described, or even utilize other types of cells, including plant cells, yeast cells, insect cells, fungi and bacteria. Thus the choice of cell type is not intended to be limiting to the invention.

The yields obtainable using the methods of the present invention depend on a number of parameters including but not limited to the culture conditions and the species of host cell used. In embodiments of the present invention, the yield preferably exceeds 50 mg/L of protein, such as more than 60 mg/L, for example more than 75 mg/L, such as more than 100 mg/L, for example more than 125 mg/L, such as more than 150 mg/L, for example more than 200 mg/L, such as more than 250 mg/L, for example more than 300 mg/L, such as more than 400 mg/L, for example more than 500 mg/L, such as more than 600 mg/L, for example more than 700 mg/L, such as more than 750 mg/L, for example more than 800 mg/L, such as more than 900 mg/L, for example more than 1,000 mg/L such as more than 2 g/L, for example more than 3 g/L, such as more than 4 g/L, for example more than 5 g/L.

The recombinant polyclonal protein of the present invention is intended to cover a protein composition comprising different, but homologous protein molecules, which are naturally variable, meaning that, in preferred embodiments, the library of variant nucleic acids comprises a naturally occurring diversity. Thus, each protein molecule is homologous to the other molecules of the composition, but also contains one or more stretches of variable polypeptide sequence, which is/are characterized by differences in the amino acid sequence between the individual members of the polyclonal protein. The differences in the amino acid sequence(s) that constitute the variable polypeptide sequence might be as little as one amino acid. Preferably the differences in the amino acid sequence constitute more than one amino acid.

Usually, the natural variability of a polyclonal antibody or TcR is considered to be located in the so-called variable regions or V-regions of the polypeptide chains.

In one aspect of the present invention individual members in a polyclonal protein comprise variable regions that are approximately between 80 and 120 amino acids long. The variable regions may comprise hyper-variable domains, e.g. complementarity determining regions (CDR).

In naturally occurring TcRs there are four CDRs in each variable region. In naturally occurring antibodies there are three CDRs in the heavy chain and three CDRs in the light chain.

In an additional aspect of the present invention the variable regions of the individual members of a polyclonal protein comprise at least one hyper-variable domain that is between 1 and 26 amino acids long, preferably between 4 and 16 amino acids long. This hyper-variable domain can correspond to a CDR3 region. For antibodies each variable region preferably constitute three hyper-variable domains. These can correspond to CDR1, CDR2 and CDR3. For TcRs each variable region preferably constitutes four hyper-variable domains. These can correspond to CDR1, CDR2, CDR3 and CDR4. The hyper-variable domains may alone constitute the variable sequences within a variable region of a recombinant polyclonal protein of the present invention.

In the context of the present invention, variability in the polypeptide sequence (the polyclonality) can also be understood to describe differences between the individual antibody molecules residing in so-called constant regions or C regions of the antibody polypeptide chains, e.g., as in the case of mixtures of antibodies containing two or more different antibody isotypes, such as the human isotypes IgG1, IgG2, IgG3, IgG4, IgA1, IgA2, IgM, IgD, and IgE, or the murine isotypes IgG1, IgG2a, IgG2b, IgG3, IgM, and IgA. Thus, a recombinant polyclonal antibody may comprise antibody molecules that are characterized by sequence differences between the individual antibody molecules in the variable region (V region) or in the constant region (C region) or both. Preferably, the antibodies are of the same isotype, as this eases the subsequent purification considerably. It is also conceivable to combine antibodies of e.g. isotype IgG1, IgG2, and IgG4, as these can all be purified together using Protein A affinity chromatography. In a preferred embodiment, all antibodies constituting the polyclonal antibody have the same constant region to further facilitate purification. More preferably, the antibodies have the same constant region of the heavy chain. The constant region of the light chain may also be the same across distinct antibodies.

In order to provide variant nucleic acid sequences that encode proteins that bind a particular antigen, a number of methods known in the art may be utilized. Typically, the invention will benefit from the use of a screening procedure that enables identification and/or isolation of nucleic acids that encode protein that bind a particular antigen. Several of these methods include an enrichment step or a so-called biopanning step, known from technologies such as Symplex™ (Mejier et al, 2006, J. Mol. Biol, 358:764-772; WO 2005/042774), phage display (Kang, A. S. et al. 1991. Proc Natl Acad Sci USA 88, 4363-4366), ribosome display (Schaffitzel, C. et al. 1999. J. Immunol. Methods 231, 119-135), DNA display (Cull, M. G. et al. 1992. Proc Natl Acad Sci USA 89, 1865-1869), RNA-peptide display (Roberts, R. W., Szostak, J. W., 1997. Proc Natl Acad Sci USA 94, 12297-12302), covalent display (WO 98/37186), bacterial surface display (Fuchs, P. et al. 1991. Biotechnology 9, 1369-1372), yeast surface display (Boder, E. T., Wittrup, K. D., 1997. Nat Biotechnol 15, 553-557) and eukaryotic virus display (Grabherr, R., Ernst, W., 2001. Comb. Chem. High Throughput. Screen. 4, 185-192), methods that are all known in the art and all are interesting aids in the practice of the present invention. FACS and magnetic bead sorting are also applicable for enrichment (panning) purposes using labeled antigen. Immunodetection assays such as ELISA (Dreher, M. L. et al. 1991. J. Immunol. Methods 139, 197-205) and ELISPOT (Czerkinsky, C. C. et. al. 1983. J Immunol Methods. 65, 109-21) can also be used either following a biopanning step or alone.

A composition of a recombinant polyclonal protein of interest comprises a defined subset of proteins, which have been defined by a common feature such as the shared binding activity towards a desired target, e.g., in the case of polyclonal antibodies against the desired target antigen. Typically a polyclonal protein composition has at least 2, 3, 4, 5, 10, 20, 50, 100, 1000, $10^4$, $10^5$ or $10^6$ distinct variant members. The number of distinct members needed in the polyclonal protein composition will depend on the complexity of the target. In the case of antibodies the complexity of the antigen(s) targeted will influence the number of distinct variant members necessary in the polyclonal antibody composition. With small or not very complex targets, for example a small protein, a polyclonal antibody composition that comprises between 2 or 3 and 100 distinct variant members may be sufficient, and it is preferred that the number of variants does not exceed 90, or even 80 or 70. In many instances, the number of distinct variants will not exceed 60 or 50, and it is preferred that the number of variants are in the range between 5 and 40, such as between 5 and 30. Whereas for more complex targets, a polyclonal antibody composition that comprises between 20 to 500 distinct variant members may be sufficient. Very complex targets, where the antigen comprises many different molecules, a polyclonal antibody composition comprising between 50 to 10,000 distinct variant members may be required.

In mammals, there are several known examples of naturally occurring polyclonal proteins either circulating freely in the blood such as antibodies or immunoglobulin molecules or present on cell surfaces such as T cell receptors and B cell receptors. The diversity of these naturally occurring polyclonal proteins are, in some mammals, achieved by genetic recombination of genes encoding variable regions of these proteins. Antibodies are further known to increase their diversity by somatic mutation. The present invention can utilize these natural diversities by isolating the sequences responsible for the diversity (e.g., the variable domains or CDR regions of immunoglobulin molecules or TcRs) and generating a library from them. For proteins encoded from two independent gene segments, e.g. antibody variable heavy chain and variable light chain, TcRα chain and β chain or TcRδ chain and γ chain, each vector in the library will constitute a pair of these variable region encoding sequences. The generation of libraries of pairs of variable region encoding sequences is well known in the art.

Libraries comprising naturally occurring diversities are for example, combinatorial libraries (random pairing of the variable region encoding sequences) as well as cognate pair libraries (pairs of variable region encoding sequences derived from the same cell, e.g. WO 2005/042774). Further libraries generated from isolated CDR gene fragments, which are incorporated into an appropriate framework (e.g. Soderlind, E. et al., 2000. Nat. Biotechnol. 18, 852-856), such as an antibody or TcR variable region are applicable with the present invention. The libraries are preferably screened to obtain sub-libraries (libraries of interest) with a desired specificity.

Diversities of proteins can also be made in an artificial way, for example synthetic or by mutation. Mutations can either be random or point mutations of a nucleic acid sequence encoding a single protein, thereby generating a polyclonal population of the single protein. Another example of generating artificial antibody libraries are described in EP 0 859 841, a method which is based on generating a library of variable region frameworks which can be combined with another library of CDRs.

In a preferred embodiment of the invention, the recombinant polyclonal protein is a recombinant polyclonal antibody or antibody fragment.

In another preferred embodiment of the invention, the recombinant polyclonal protein is a recombinant polyclonal TcR or TcR fragment.

A recombinant polyclonal protein of the present invention can therefore also be constituted of the different isotypes or more preferred of different subclasses. Polyclonality of the immunoglobulins can occur in the constant part or in the variable domain of the immunoglobulin molecule or in both the constant part and the variable domain.

Polyclonality in the so-called constant region, particularly the heavy chain of the antibodies, is of interest with regard to therapeutic application of antibodies. The various immunoglobulin isotypes have different biological functions (summarized in Table 1), which might be desirable to combine when utilizing antibodies for treatment because different isotypes of immunoglobulin may be implicated in different aspects of natural immune responses (Canfield and Morrison 1991. J. Exp. Med. 173, 1483-91; Kumpel et al. 2002. Transfus. Clin. Biol. 9, 45.-53; Stimadel et al. 2000. Epidemiol. Infect. 124, 153-162).

TABLE 1

Biological functions of the human immunoglobulin isotypes

| | Human Immunoglobulin | | | | | | | | |
|---|---|---|---|---|---|---|---|---|---|
| | $IgG_1$ | $IgG_2$ | $IgG_3$ | $IgG_4$ | $IgA_1$ | $IgA_2$ | IgM | IgD | IgE |
| Classical complement activation | +++ | ++ | ++++ | + | – | – | ++++ | – | – |
| Alternate complement activation | + | + | + | +++ | + | – | – | + | – |
| Placental transfer | + | ++ | + | ++ | – | – | – | – | – |
| Bacterial lysis | + | + | + | + | +++ | +++ | + | ? | ? |
| Macrophage/other phagocytes binding | + | – | + | + | + | + | – | – | – |
| Mast cell/basophils binding | – | – | – | – | – | – | – | – | – |
| Staphylococcal Protein A reactivity | + | + | – | + | – | – | – | – | – |

A further aspect of the present invention is a recombinant polyclonal manufacturing cell line, comprising a polyclonal cell line comprising 2-n populations of cells each population expressing a distinct member of a recombinant polyclonal protein, the cells comprising expression constructs randomly integrated the genome. The expression constructs are preferably stably integrated into the genome. The constructs in one embodiment are integrated into one or more chromosomes.

The number of populations of cells in the polyclonal cell line, n, may be 3 or more, such as 4 or more, for example 5 or more, such as 6 or more, for example 7 or more, such as 8 or more, for example 9 or more, such as 10 or more, for example 11 or more, such as 12 or more, for example 13 or more, such as 14 or more, for example 15 or more, such as 16 or more, for example 17 or more, such as 18 or more, for example 19 or more, such as 20 or more, for example 21 or more, such as 22 or more, for example 23 or more, such as 24 or more, for example 25 or more, such as 26 or more, for example 27 or more, such as 28 or more, for example 29 or more, such as 30 or more, for example 35 or more, such as 40 or more, for example 45 or more, such as 50 or more, for example 60 or more, such as 70 or more, for example 80 or more, such as 90 or more, for example 100 or more.

For most purposes n may be less than 50, such as less than 45, for example less than 40, such as less than 35, for example less than 30.

One important embodiment of the present invention is the cell cloning step performed prior to finally mixing the polyclonal cell line. This step results in improved yield and stability of the obtained polyclonal cell banks by minimizing the occurrence of clonal bias. Cells expressing one distinct member of the recombinant polyclonal protein may be derived from 1 or more cloned cells, such as from 2 or more, for example from 3 or more, such as from 4 or more, for example from 5 or more, such as from 6 or more, for example from 7 or more, such as from 8 or more, for example from 9 or more, such as from 10 or more for example 11 or more, such as 12 or more, for example 13 or more, such as 14 or more, for example 15 or more, such as 16 or more, for example 17 or more, such as 18 or more, for example 19 or more, such as 20 or more, for example 21 or more, such as 22 or more, for example 23 or more, such as 24 or more, for example 25 or more, such as 26 or more, for example 27 or more, such as 28 or more, for example 29 or more, such as 30 or more, for example 35 or more, such as 40 or more, for example 45 or more, such as 50 or more, for example 60 or more, such as 70 or more, for example 80 or more, such as 90 or more, for example 100 or more. For most purposes the number of cloned cells is less than 50, for example less than 20, such as less than 15, for example less than 10.

In an additional embodiment of the above embodiment the variant nucleic acid sequences encoding the polyclonal protein (preferably from the immunoglobulin superfamily) are all derived from naturally occurring sequences, for example isolated from a donor.

Clonal Diversity

One of the characteristics of a polyclonal protein is that it is constituted by a number of individual protein molecules where each protein molecule is homologous to the other molecules of the polyclonal protein but also has a variability that is characterized by differences in the amino acid sequence between the individual members of the polyclonal protein. Preferably, the differences are confined to distinct areas of the overall structure of the polyclonal protein. Such areas are for example the variable region of an antibody or TcR and possibly further confined to the CDR regions in these areas. This variability can also be described as a diversity, which can be identified both on the nucleic acid level as well as on the protein functional level, e.g., specificity and affinity differences towards a target.

Clonal diversity of the cell line may be analyzed by RFLP on isolated clones from a pool of cells expressing a recombinant polyclonal protein. Sequencing of (RT)-PCR products represents another possibility to analyse clonal diversity. The diversity can also be analyzed by functional tests (e.g., ELISA) on the recombinant polyclonal protein produced by the cell line. WO 2006/007853 discloses methods for characterization of a polyclonal cell line and a polyclonal protein. These methods can be used for analyzing the clonal diversity of the cell line and the resulting polyclonal protein.

Clonal bias (i.e., a gradual change in the content of the individual antibodies constituting the polyclonal antibody), if it exists, can be estimated by comparing the clonal diversity of the initial library, used for transfection, with the diversity found in the pool of cells (cell line) expressing the recombinant polyclonal protein.

Clonal diversity of a polyclonal protein expressed from a cell line may be assessed as the target coverage by the polyclonal protein. In this case sufficient diversity is considered to be acquired when approximately 25-100% of the desired target molecules are bound by the polyclonal protein. For example in the case of a polyclonal antibody, the binding of antibody to at least 25% of the non-identical epitopes on the surface of a target antigen provides a sufficient diversity in the composition. Preferably, clonal diversity by target coverage is at least 50%, and even more preferable at least 75%. For antibodies, such a target coverage could for example be assessed by epitope mapping.

Alternatively clonal diversity can be assessed as the distribution of individual members of the polyclonal composition. This distribution can be assessed as the total number of different individual members in the final polyclonal protein composition compared to the number of different encoding sequences originally introduced into the cell line during transfection. In this case sufficient diversity is considered to be acquired when at least 50% of the encoding sequences originally used in the transfection can be identified as different individual members of the final polyclonal proteins, preferably at least 75%, more preferably at least 80%, more preferably at least 90%, such as at least 95%, 97%, 98% or 99%. Expressed in another way, clonal diversity can be considered sufficient if only 1 member of the polyclonal protein is lost during manufacture, or if 2, 3, 4 or 5 members are lost.

The distribution of individual members of the polyclonal composition can also be assessed with respect to the mutual distribution among the individual members. In this case sufficient clonal diversity is considered to be acquired if no single member of the composition constitutes more than 75% of the total amount of protein in the final polyclonal protein composition. Preferably, no individual member exceeds more than 50%, even more preferred 25% and most preferred 10% of the total number of individual members in the final polyclonal composition. The assessment of clonal diversity based on the distribution of the individual members in the polyclonal composition can be performed by RFLP analysis, sequence analysis and protein analysis such as the approaches described later on for characterization of a polyclonal composition.

Clonal diversity may be reduced as a result of clonal bias which can arise a) as a result of differences in expression level, b) as a result of variations in cellular proliferation. If such biases arise, each of these sources of a loss of clonal diversity is easily remedied by minor modifications to the methods as described herein.

It is possible that variations in cellular proliferation rates of the individual cells in the cell line could, over a prolonged period of time, introduce a bias into the recombinant polyclonal protein expression, increasing or reducing the presence of some members of the recombinant polyclonal protein expressed by the cell line. As the present methods may be based on random integration into the genome of the host cell, both the position and the copy number vary between members of the polyclonal cell line. This is likely to give rise to differences in proliferation rate and expression level among clones. By selecting cellular clones with similar proliferation rate this problem is minimized. A further possibility is to use more than one clone for each member of the polyclonal protein. The examples illustrate that the compositional stability is increased if say between 3 and 5 clones expressing a single member of the polyclonal protein is used compared to only one clone for each member of the polyclonal protein.

Another way to address this issue is to use one or more selection criteria to ensure that the cells are uniform within certain pre-set limits with respect to one or more criteria selected from the group consisting of growth rate, doubling time, expression level, production level, stability of production over time, viability, hardiness, robustness, morphology, and copy number.

One reason for variations in proliferation rates could be that the population of cells constituting the starting cell line used for the initial transfection is heterogeneous. It is known that individual cells in a cell line develop differently over a prolonged period of time. To ensure a more homogeneous starting material, sub-cloning or repeated sub-cloning of the cell line prior to transfection with the expression vectors of interest may be performed using a limiting dilution of the cell line down to the single cell level and growing each single cell to a new population of cells (so-called cellular sub-cloning by limiting dilution).

An alternative and preferred method for single cell cloning to ensure a well defined cell population is to use fluorescence activated cell sorting (FACS) after the transfection. This may be done prior to the selection procedure. Fluorescence labeled antibodies can be used to enrich for highly productive cells derived from a pool of cells transfected with IgG constructs (Brezinsky et al. J. 2003. Immunol Methods 277, 141-155). The advantage of using FACS sorting is that the method combines single cell cloning (by sorting single cells into wells), while simultaneously providing information about the expression level of each single cell. To further improve the sorting procedure, a viability stain can be included so that dead or dying cells are discarded. The FACS procedure subjects cells to rather severe conditions including shear stress. This means that indirectly cells are selected for resistance to such conditions. Furthermore, the FACS procedure is automated allowing for sorting of a high number of single cells.

The FACS method can also be used to sort cells expressing similar levels of immunoglobulin, thereby creating a homogenous cell population with respect to productivity. Likewise, by using labeling with the fluorescent dye 5,6-carboxylfluorescein diacetate succinimidyl ester (CFSE) cells showing similar proliferation rates can be selected by FACS methods.

An important embodiment of the present invention is the generation of one or more cloned cell lines for each member of the polyclonal antibody. The generation of single cell clones may be carried out using any one of a number of standard techniques. However, it has turned out that FACS cell sorting where cells are selected for viability and IgG levels and are sorted individually into wells has consistently turned out to provide stable clones suitable for preparing a polyclonal master cell bank and a subsequent polyclonal working cell bank. The selection pressure from e.g. Mtx may be removed prior to or during the FACS sorting, but a continued selection pressure, e.g. by growing in a nucleoside free medium is preferably maintained. Individual clones are preferably selected after a certain number of days in culture under selection pressure following the cell sorting. As clones are selected on the same day following sorting, the growth rate of the clones will be relatively uniform. In addition to this colonies are inspected visually to discard clones with gross changes in morphology and low growth rates compared to the original untransfected cell line. Finally, the level of antibody expression can be assayed using e.g. ELISA or other analytical techniques and clones with high and relatively uniform expression levels can be selected.

Even if a proliferation rate-induced bias does develop, the loss or over-representation of individual members may not necessarily be critical, depending on the diversity requirements of the final recombinant polyclonal protein product and the stability of the diversity over time.

The Host Cell

Host cells can be generated from any cell which can integrate DNA into their chromosomes or retain extra-chromosomal elements such as mini-chromosomes, YACs (Yeast artificial chromosomes), MACs (Mouse artificial chromosomes), or HACs (Human artificial chromosomes). MACs and HACs are described in detail in WO 97/40183, hereby incorporated by reference. Preferably mammalian cells such as CHO cells, COS cells, BHK cells, myeloma cells (e.g., Sp2/0, YB2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fingi, E. coli etc., can also be employed.

In one embodiment of the present invention, the cell line which is to be used as starting material is sub-cloned by performing a so-called limiting dilution of the cell line down to a single cell level, followed by growing each single cell to a new population of cells prior to transfection with the library of vectors of interest. Such sub-cloning can also be performed later in the process of selecting the right cell line, if desired. Other methods for single cell cloning include: FACS cloning (Brezinsky et al. J. 2003. Immunol Methods 277, 141-155), LEAP™ technology (from Cyntellect, San Diego, Calif., USA), and ClonePix (from Genetix, UK).

The Vector for Integration

The following description focuses on the use of mammalian expression systems. However, it is likewise possible to use the methods of the invention for expression in bacteria with suitable modifications.

A suitable vector comprises a suitable selection gene. Suitable selection genes for use in mammalian cell expression include, but are not limited to, genes enabling for nutritional selection, such as the thymidine kinase gene (TK), glutamine synthetase gene (GS), tryptophan synthase gene (trpB) or histidinol dehydrogenese gene (hisD). Further, selection markers are antimetabolite resistance genes conferring drug resistance, such as the dihydrofolate reductase gene (dhfr) which can be selected for with hypoxanthine and thymidine deficient medium and further selected for with methotrexate, the xanthine-guanine phosphoribosyltransferase gene (gpt), which can be selected for with mycophenolic acid, the neomycin phosphotransferase gene (neo) which can be selected for with G418 in eukaryotic cell and neomycin or kanamycin in prokaryotic cells, the hygromycin B phosphotransferase (hyg, hph, hpt) gene which can be selected for with hygromycin, the puromycin N-acetyl-transferase gene (pac) which can be selected with puromycin or the Blasticidin S deaminase gene (Bsd) which can be selected with blasticidin, the Zeocin resistance gene (Sh ble) which mediates resistance towards Zeocin and Bleomycin. Finally, genes encoding proteins that enables sorting e.g. by flow cytometry can also be used as selection markers, such as green fluorescent protein (GFP), the nerve growth factor receptor (NGFR) or other membrane proteins, or beta-galactosidase (LacZ).

The selection marker may be located on a separate expression vector, thus performing co-transfection with an expression vector coding for the selection marker and one or more expression vector(s) coding for the protein of interest or sub-units of the protein of interest. The selection marker may also be located in the expression vector coding for the protein of interest. In this latter case, the selection marker is preferably located on a transcript which also encodes the protein of interest or one of its sub-units. This can be done e.g. using an IRES construct. In the case of a multimeric protein, such as an antibody, the selection marker is preferably located on the transcript which encodes the largest sub-unit, such as for example the heavy chain of an antibody.

The vector for integration of the gene of interest further comprises DNA encoding one member of the recombinant polyclonal protein of interest, preceded by its own mammalian promoter directing expression of the protein. If a member of the recombinant polyclonal protein of interest comprises more than one protein chain, e.g., if the member is an antibody or T cell receptor, the DNA encoding the chains of the protein can be preceded by their own mammalian promoter directing high levels of expression (bi-directional or uni-directional) of each of the chains. In a bi-directional expression a head-to-head promoter configuration in the expression vector can be used and for a uni-directional expression two promoters or one promoter combined with e.g., an IRES sequence can be used for expression. A bi-cistronic expression vector with two different subunits encoded by the same transcript and separated by an IRES sequence is likewise conceivable.

Suitable head-to-head promoter configurations are for example, but not limited to, the AdMLP promoter together with the mouse metallothionein-1 promoter in both orientations, the AdMLP promoter together with the elongation factor-1 promoter in both orientations or the CMV promoter together with the MPSV promoter in both orientations, or the CMV promoter used in both orientations.

In the case of antibodies, experience has shown that the amount of heavy chain expressed by a cell should not exceed the amount of light chain. Therefore, the promoter directing expression of the light chain is preferably at least as strong as the promoter directing expression of the heavy chain.

A nucleic acid sequence encoding a functional leader sequence or translocation signal can be included in the expression vector to direct the gene product to the endoplasmic reticulum or a specific location within the cell such as an organelle. A strong polyadenylation signal can be situated 3' of the protein-encoding DNA sequence. The polyadenylation signal ensures termination and polyadenylation of the nascent RNA transcript and is correlated with message stability. The DNA encoding a member of the recombinant polyclonal protein of interest can, for example, encode both the heavy and light chains of an antibody or antibody fragments, each gene sequence optionally being preceded by their own mammalian promoter elements and/or followed by strong poly A signals directing high level expression of each of the two chains.

The expression vector for integration can carry additional transcriptional regulatory elements, such as enhancers, anti-repressors, or UCOE (ubiquitous chromatin opening elements) for increased expression and stability of expression at the site of integration. Enhancers are nucleic acid sequences that interact specifically with nuclear proteins involved in transcription. The UCOE opens chromatin or maintains chromatin in an open state and facilitates reproducible expression of an operably-linked gene (described in more detail in WO 00/05393 and Benton et al, Cytotechnology 38:43-46, 2002). Further enhancers or enhancing elements include Matrix Attachment Regions (MARs) as described e.g. in Girod & Mermod 2003 ("Chapter 10: Use of scaffold/matrix-attachment regions for protein production", pp 359-379 in Gene Transfer and Expression in Mammalian Cells, S C Makrides (ed), 2003, Elsevier Science BV). Anti-repressor elements include but are not limited to STAR elements (Kwaks et al Nat. Biotechnol. 2003 May; 21(5):553-8). When one or more of the regulatory elements described in the above are integrated into the chromosome of a host cell they are termed heterologous regulatory elements.

Polyclonal Working Cell Banks and Master Cell Banks

In preferred embodiments of the invention, use is made of polyclonal Morking Cell Banks (pMCB) and polyclonal Waster Cell Banks (pWCB).

A pMCB which can be used for the establishment of the polyclonal manufacturing cell line by thawing and expanding the contents of a single ampoule, may be generated from a frozen stock composed of individual cell lines. The individual cell lines used to generate such a pMCB are either obtained from i) a single clone (as described in Example 2), ii) a mixture of single clones (as described in Example 2), or iii) a pool of clones (a pool of single colonies obtained after selection). The clones have been obtained from host cells individually transfected with, and selected for stable expression of an individual member of a polyclonal protein. Selection for stable expression is performed by procedures known in the art, e.g. using selection marker genes. In a preferred embodiment of the present invention the individual cell lines are obtained from cloned or subcloned cells, e.g. by subjecting a cell line originating from i) ii) or iii) to limiting dilution or single cell FACS analysis and selection, or by selecting high expression clones e.g. using a robot like the ClonePix FL (see below). The individual cell lines used to generate the pMCB as described above may be pre-stored in a frozen library stock of individual cell lines, from which an ampoule of each individual cell line is thawn and expanded prior to the generation of a pMCB. Preferably, the individual cell lines express full-length antibodies with properties that differ from the properties of the antibodies produced by the other members of the pMCB, e.g. different antigen specificity, different affinity, different variable or CDR regions and/or different constant regions.

Each cell line used to generate the pMCB, produces a different member of a polyclonal protein. Preferably, each distinct member of the polyclonal protein binds a particular antigen. Additionally, it is preferred that each distinct member is produced from multiple integrants located at random sites in the genome of each host cell. A pMCB is generated by mixing a predefined number of cells from each individual cell line. Preferably, the cells are mixed in equal numbers (a 1:1 ratio), although other ratios also may be desired (see later). The mixture of cells is frozen down in aliquots, in that they are distributed into a number of vials with a defined number of cells in each vial. These vials are frozen and stored as the pMCB for later manufacturing purposes. Preferably, the number of vials constituting the pMCB exceeds 10, 25, 50, 75, 100, 200, 500 or 1000 vials. The individual vials in a pMCB may be thawn at different points in time generating different batches of the polyclonal manufacturing cell line which are capable of producing a polyclonal protein with essentially the same composition from batch to batch.

In an alternative approach of the present invention, the polyclonal manufacturing cell line may be expanded from a pWCB, which is derived from a pMCB. The pWCB is generated by thawing a single vial from a pMCB and expanding the cells for a number of generations sufficient to produce a total number of cells which can be frozen down in a new series of aliquots (the pWCB), with approximately the same number of cells in each pWCB aliquot as in the pMCB vial originally used to generate the pWCB. When the pWCB has been exhausted, it is possible to generate a new pWCB from an aliquot of the pMCB. This approach will therefore require a significantly lower amount of work than would be required to expand the individual cell lines from the frozen library stock and mixing a new pMCB. Further, in the event that the pWCB is exhausted, the chance of producing further batches of the polyclonal manufacturing cell line, which are capable of producing a polyclonal protein with essentially the same composition from batch to batch is increased.

An advantage of producing a pMCB by mixing individual cell lines which have been obtained by individual transfection is that it is possible to perform additional analysis and selections of the individually transfected cell lines prior to generation of the pMCB. This may ensure a more stable polyclonal manufacturing cell line which fulfills the diversity requirements already described. In addition the polyclonal protein may be manufactured in a more reproducible way.

What is said in the following regarding pMCB also applies to pWCB.

In an additional embodiment of the present invention, individual cell lines which have been selected for stable expression of an individual member of a polyclonal protein as described above, are further characterized with respect to their proliferation rates and/or productivity prior to generation of a pMCB. In a preferred embodiment cell lines with similar proliferation rates or productivity are selected for the generation of a pMCB. Even more preferred, cell lines with similar productivity as well as similar proliferation rates are selected for the generation of the pMCB. Preferably, the cell lines are adapted to serum free suspension culture prior to the characterization of proliferation rates and/or productivity. Alternatively, the parental cells used for transfection are adapted to serum free suspension culture prior to transfection.

Proliferation rates can be assessed by methods known in the art. Proliferation rates for mammalian cell lines should be between 18 and 100 hours, preferably between 22 and 40 hours and most preferred between 24 and 32 hours. The productivity should exceed 0.5 pg protein per cell per day (pg/(cell*day)), preferably it should exceed 1, 1.5, 3, 5, 8, 10, 15, 20, 30, 40, 50. 75, or 100 pg/(cell*day). Further, the cell line should show a homogenous cell population with respect to expression when assessed by an intra-cellular staining method. If desired a more homogeneous cell population for each individual cell line can be obtained by cloning e.g. by the FACS sorting methods described herein.

In further embodiments of the present invention, the individual cell lines are FACS sorted to identify cells with a homogeneous expression level, after the transfection and selection procedures as described herein.

Fluorescence labeled antibodies can be used to sort for cells expressing high levels of the desired protein e.g. antibody or TcR, thereby creating a homogeneous cell population with respect to productivity. This technique is based on the observation that secreted proteins can be detected on the surface of the cell secreting them, and the amount of surface protein apparently corresponds to the expression levels of the individual cell. The high producing cells can therefore be single cell sorted upon staining with a labeled antibody, followed by analysis by FACS. The technique has been described by Brezinsky (Brezinsky et al. J. 2003. Immunol Methods 277, 141-155).

An alternative sorting technique is based on the coupling of a ligand, with specificity to the protein expressed from the cells, to the surface of the cells. For example an anti-Fc antibody or an anti-idiotype antibody can be coupled to the surface of the protein secreting cell population via biotin. The antibodies secreted by an individual cell are then captured by the anti-Fc antibodies on the surface of that cell. Following this, the high producing cells can be sorted by FACS upon staining with a labeled antibody. This technique has been described in EP 667 896.

To obtain cell lines with a homogeneous high expression levels, single cells having a high expression level are analyzed based on the FACS profile obtained by one of the described techniques. The individual cell clones are then expanded and potentially analyzed with respect to proliferation rates and productivity as described above. Alternatively, a sub-pool of cells having the highest expression level as identified by the FACS profile is collected by sorting. The sub-pool of cells from the individual cell line can likewise be analyzed with respect to proliferation rates and productivity if desired.

In an alternative embodiment of this invention, a robot such as the ClonePixFL robot (Genetix, UK) is used to select clones exhibiting high expression levels and/or similar growth properties. This is done as follows: The colonies obtained after transfection and selection are grown in a semi-solid medium which allows for detection of high-producing colonies by capturing the secreted protein product in the immediate proximity of the colony. The production level from each colony is determined by means of immunofluorescence labeling of the protein expressed by the cells followed by image software selection of the best clones based on pre-determined selection criteria such as expression level and growth properties. Furthermore, the size (reflecting the cell proliferation rate) of each colony can be assessed by the robot using light detection imaging. Colonies with the desired production and/or growth properties are then isolated by the robot and transferred to 96-well plates for further propagation.

Preferably, individual cell lines with similar productivity are selected for the generation of the pMCB. In a preferred embodiment individual cell lines constituting the pMCB are generated from cloned cells, e.g. obtained by single cell sorting, limiting dilution or robot picking, with a high expression level or from a pool of cells with high expression level.

In the present invention, both individual cell lines obtained from a single colony of cells isolated after transfection and selection as well as individual cell lines obtained from a clone obtained e.g. by single cell FACS sorting, are termed cloned cell lines. In a preferred embodiment such cloned cell lines are used to generate the pMCB.

In further embodiments of the present invention, the individual cell lines are mixed at different ratios upon generation of a pMCB. The individual cell lines can be mixed according to predetermined criteria based on the properties of the individual cell lines and/or individual protein member expressed by said cell line, e.g. specific productivity or binding affinity. For example, individual cell lines expressing certain antibodies binding particularly critical antigens or epitopes can be supplied in excess of the remaining member cell lines of the pMCB, e.g. in 2-fold, 3-fold, 5-fold or 10-fold higher amounts. One member cell line may for example be added in a 2:1 ratio over all the other members, e.g. $4 \times 10^6$ cells of member 1 and $2 \times 10^6$ cells of each of the remaining member cell lines.

This approach of differentiated ratios of the individual cell lines in the pMCB may also be adopted to circumvent differences in proliferation rates and productivity among the individual cell lines, in particular if these have not been selected for similarity in these traits. Hence, if one or more of the individual cell lines have a slower proliferation rate, i.e. longer doubling times, compared to other members of the polyclonal working cell bank which are characterized by a faster proliferation rate, but this slower proliferation rate is not associated with a particular high productivity, this particular member(s) may be added to the pMCB in an increased amount to compensate for its slow growth. For example a cell line with a proliferation rate of 50 hours may be added in a 2:1 ration if the remaining cell lines constituting the pMCB have proliferation rates between 22 and 30 hours. Likewise, the ratio of cell lines with short doubling times may be reduced to ensure that these will not take over during manufacturing. Further, the ratios of the individual cell lines in a pMCB may be adjusted upon analysis of the polyclonal protein products produced from the polyclonal manufacturing cell lines generated from the pMCB. Such adjustments may for example be made based on IEX profiles or equivalent characterization tools. If such an analysis shows that one or more particular protein members are produced in an increased amount compared to the remaining members, a new pMCB may be generated, wherein the ratio of the cell lines producing these particular protein members are reduced. And visa versa, if a particular member is produced in a low amount, a pMCB with an increased ratio of the cell line producing this member may be generated.

Culture Systems

The recombinant polyclonal protein of the invention may be manufactured using any suitable cultivation mode including but not limited to batch, fed-batch and perfusion processes.

Establishing an Expression System for High-Level Expression of Proteins

Methods for introducing a nucleic acid sequence into a cell are known in the art. These methods typically include the use of a DNA vector to introduce the sequence of interest into the cell, the genome or an extra-chromosomal element. Transfection of cells may be accomplished by a number of methods known to those skilled in the art, including lipofection, chemically mediated transfection, calcium phosphate precipitation, electroporation, microinjection, liposome fusion, RBC ghost fusion, protoplast fusion, virus transduction, and the like.

For the transfection of a host cell line, a library of vectors of interest, wherein each vector comprises only one copy of a nucleic acid sequence encoding one member of a recombinant polyclonal protein of interest, is used. This library of expression vectors of interest collectively encodes the recombinant polyclonal protein of interest. Suitable vectors for integration were described in the previous section.

The generation of a recombinant polyclonal manufacturing cell line and the production of a recombinant polyclonal protein from such a cell line can be obtained by several different transfection and manufacturing strategies.

Figure 1:
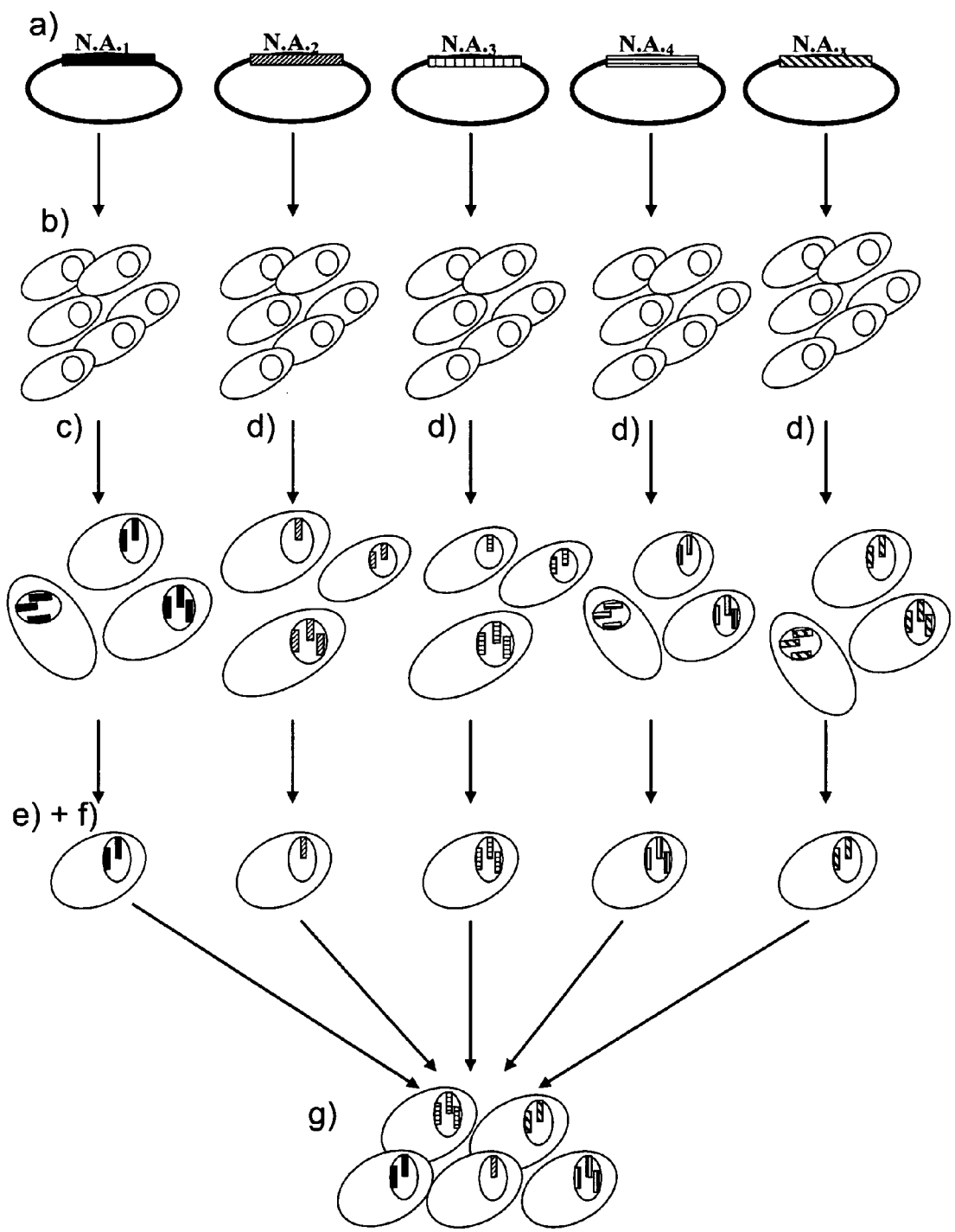
FIG. 1. Schematic overview of the process for generating a polyclonal cell bank.

A preferred way of transfection illustrated in FIG. 1, is a high throughput method in which host cells are transfected separately using the individual vectors constituting the library of interest. This method is termed individual transfection. The individually transfected host cells are preferably selected separately. However, they may also be pooled before selection. The individual cell clones generated upon selection may be analyzed with respect to expression level, proliferation rate and integration pattern and preferably, those with similar growth rates, similar copy number, similar expression and/or similar robustness levels may be used to generate a polyclonal GOI library stock. The individual cell clones can be mixed to obtain the desired polyclonal cell line before generating the stock, immediately after they have been retrieved from the stock, or after a short proliferation and adaptation time. This approach may further improve compositional stability.

Under transfection circumstances allowing integration of more than one copy into each cell, bulk transfection using mixtures of expression vectors can be performed if the polyclonal protein is a monomer. For multimeric proteins, such bulk transfection allowing multiple integration into the genome of a host cell, would result in scrambling of the subunits. In many cases, such as the manufacture of recombinant polyclonal antibody for pharmaceutical use, scrambling is to be avoided. For multimeric proteins, bulk transfection can be done if scrambling is acceptable or if transfection is carried out under conditions ensuring integration of only one copy into the genome of each host cell. Examples of such methods include retroviral transduction and sphaeroblast fusion. The individual vectors constituting the library of variant nucleic acid sequences of interest can either be mixed together into a single composition, or preferably the individual vectors encoding each library member can be kept in separate compositions or in mixtures of approximately 5 to 50 individual vectors of the library in a composition.

Another way is to use a library of vectors split into fractions, containing approximately 5 to 50 individual vectors of the library in a composition, for transfection. Preferably, a fraction of the library constitutes 10 to 20 individual vectors. Each composition is then transfected into an aliquot of host cells. This method is termed semi-bulk transfection. The number of aliquots transfected will depend on the size of the library and the number of individual vectors in each fraction. If the library for example constitutes 100 distinct variant members, which are split into fractions containing 20 distinct variant members in a composition, 5 aliquots of host cells would need to be transfected with a library composition constituting a distinct fraction of the original library. The aliquots of host cells are selected following transfection. Preferably, the distinct aliquots are selected separately. However, they can also be pooled before selection. The aliquots can be analyzed for their clonal diversity and only those with sufficient diversity will be used to generate a polyclonal GOI library stock.

A frozen stock of the polyclonal cell line may be generated before initiation of the recombinant polyclonal protein manufacturing. To obtain the desired polyclonal cell, line for manufacturing, the clones can be mixed before generating the freezing stock, immediately after they have been retrieved from the stock or after a short proliferation and adaptation time.

A shared feature in the manufacturing strategies outlined in the above is that all the individual members constituting the recombinant polyclonal protein can be produced in one, or a limited number of containers, such as bioreactors, with approximately 10 as the maximum.

If expression levels need to be increased, gene amplification can be performed using selection for a DHFR gene or a glutamine synthetase (GS) gene, a hprt (hypoxanthin phosphoribosyltransferase) or a tryptophan synthetase gene. This requires the use of vectors comprising such a selection marker. One particular feature of the present invention is to keep the copy number relatively low in order to keep the stability of the cells high. Therefore, cells are preferably only subjected to one round of selection under relatively modest selection pressure in nucleoside free medium with a low concentration of MTX (e.g. 1-10 nM) for the type of construct used in the examples. Such modest selection pressure is believed to lead to a relatively low copy number. Modest selection pressure is believed to lead to a balanced copy number resulting in high expression while avoiding the instability of cells with very high copy number.

In order to achieve higher expression levels, the cell line used for expression preferably includes a heterologous transactivator capable of enhancing the promoter controlling expression of the polyclonal protein. Examples of suitable combinations of transactivator and promoter are mentioned in the following table (Table 2).

TABLE 2

Examples of transactivator/promoter pairs

| Transactivator | Promoter Examples | Comments |
| --- | --- | --- |
| lentivirus Tat | long terminal repeat (LTR) | |
| adenovirus E1A | HCMV major IE enhancer/promoter | |
| herpes simplex virus VP16 | herpes simplex virus gene promoter is IE175 | U.S. Pat. No. 6,635,478 |
| hepatitis B virus X protein (HBx) | SV40early | |
| Synthetic Zn-finger proteins | Synthetic | Sangamo inc |
| SV40 largeT antigen | SV40 late promoter | |
| tetracycline-controlled transactivators (tTA) | Synthetic | Synthetic fusions |
| Human cytomegalovirus IE2p86 | HCMV major IE enhancer/promoter | |
| Human cytomegalovirus IE1p72 | HCMV major IE enhancer/promoter | |
| Epstein-Barr virus R transactivator (Rta) | EBV promoter | |
| thyroid hormone receptors | growth hormone promoter | |
| glucocorticoid hormone receptors | mammary tumor virus (MMTV) promoter | |

Preferably, the cell line is transfected with an expression construct coding for the transactivator and clones are selected using limiting dilution or other methods for single cell cloning. The expression vector may comprise elements such as promoter, selection marker etc as described for expression vectors herein. Preferably the promoter controlling expression of the transactivator is a constitutive promoter such as Elongation factor 1 promoter, CMV promoter, metallothionein-1 promoter or similar. In a preferred embodiment, the promoter is the CMV promoter.

Particularly preferred is the use of the adenovirus E1A transactivator, which appears to stabilize the cells on its own in addition to transactivating a CMV promoter controlling expression of the gene of interest. As mentioned elsewhere, E1A expression was not detectable in the first produced cell line, ECHO. Therefore the link between E1A and stabilization of the cells has not been proven by the present experiments.

For the manufacturing of a polyclonal protein, where each protein member is comprised of more than two polypeptide chains, the combination of the chains may be of importance for the affinity, specificity and activity of the protein they form. This is for example seen for antibodies and TcRs. For example, is the combination of antibody variable heavy chain and variable light chain known to affect affinity and specificity of an antibody formed from the chains. Thus, when a library of antibody encoding sequences has been selected for their ability to produce antibodies with affinity to a certain target it is desirable to ensure that the combination of the variable heavy chain and variable light chain in the final product corresponds to this. For this reason the polypeptide chains constituting an individual member of the polyclonal protein are preferably placed in the same vector used for integration, thereby ensuring that they will be kept together throughout the process. Alternatively, the host cells can be transfected with pairs of expression vectors coding for cognate pairs of heavy and light chain.

The following description is one example of how to obtain a recombinant polyclonal antibody expressing cell line.

A universal promoter cassette for constitutive expression having two promoters placed in opposite transcriptional direction, such as a head-to-head construction surrounded by the variable heavy chain and the whole of the kappa or lambda light chain may be constructed, allowing transfer of the whole construct into a vector comprising a selection marker and the heavy chain constant region. It is contemplated that a promoter cassette for inducible expression can also be used. Furthermore, the promoters can be placed tail-to-tail which will result in transcription in opposite direction or tail-to-head for unidirectional transcription. An inducible promoter can also be used for control of the expression. After transfection, the cells are preferably cultivated under selective conditions to select stable tranformants.

Cells that survive under these conditions can subsequently be grown in different culture systems, such as conventional small culture flasks, Nunc multilayer cell factories, small high yield bioreactors (MiniPerm, INTEGRA-CELLine), shaker, and spinner flasks to hollow fiber- and bioreactors WAVE bags (Wave Biotech, Tagelswangen, Switzerland) or other disposable vessels/containers. The cells may be tested for antibody production using ELISA. Polyclonal cell lines are preferably selected for viability in suspension growth in serum free medium under selection pressure for extended periods.

Evaluation of the Preservation of Polyclonality in the Expression System

According to the present invention, it is often important to ensure that the polyclonality in the expression system is not seriously altered during production so that it is possible to stop the production when polyclonality is indeed altered. This is according to the invention done by monitoring the relative expression levels of the variant nucleic acid sequences. The expression levels can for example be monitored at mRNA level using for example RFLP analysis, arrays or real-time PCR, or at the protein level using for example two-dimensional polyacrylamide gel electrophoresis, mass spectrometry or various chromatographic techniques. With these techniques it will be possible to establish a baseline value for a number of all of the individual expression levels and then take out samples from the culture during production in order to gauge whether expression levels have changed (both in total and relatively). In normal practice of the invention, a range of values surrounding the baseline values can be established, and if the relative expression levels are found to be outside the ranges, then production is terminated.

Cultivation of Cells and Production of a Recombinant Polyclonal Antibody

The polyclonal cell line produced as described above may be grown in suitable media under suitable conditions for expressing the polyclonal protein of interest encoded by the variant nucleic acid sequences inserted into the genome of the cells. The cell cultivation may be performed in several steps. When using mammalian cells, the selected cells are preferably adapted to growth in suspension as well as serum free conditions. Adaptation to growth in serum free medium may also advantageously be done before mixing the cloned cell lines for the polyclonal cell line. Adaptation can be performed in one or two steps and with or without selection pressure.

Preferably, a selection system is used which allows for selection throughout the manufacturing period without compromising the purity of the manufactured drug product. In general, for manufacture of recombinant proteins for pharmaceutical use it is preferred not to use e.g. antibiotics or other low molecular weight drugs to provide selection pressure, as it will be needed to validate that the final product does not contain any traces of the antibiotic.

When the polyclonal cell line is adapted to the appropriate conditions scaling up can be initiated. At this point a polyclonal working cell stock (polyclonal working cell bank, pWCB) and/or polyclonal master cell bank (pMCB) can be frozen down. Preferably bioreactors of between 30 and 100 liters are used, but smaller (5-10 liters) or larger (up to 1,000, 5,000, 10,000, 15,000 liters, or even larger) bioreactors may be employed. The suitable production time and choice of bioreactor size are dependent on the desired yield of protein from the batch and expression levels from the cell line. Times may vary from a couple of days up to three months. The expressed recombinant polyclonal protein may be recovered from the cells or the supernatant. The recombinant protein may be purified and characterized according to procedures known by a person skilled in the art. Examples of purification procedures are listed below. Examples of characterization procedures can be found in e.g. WO 2006/007853.

Purification of a Recombinant Polyclonal Protein from Culture Supernatant

Isolation of specific proteins from culture supernatants is possible using various chromatographic techniques that utilize differences in the physico-chemical properties of proteins, e.g. differences in molecular weight, net charge, hydrophobicity, or affinity towards a specific ligand or protein. Proteins may thus be separated according to molecular weight using gel filtration chromatography or according to net charge using ion-exchange (cation/anion) chromatography or alternatively using chromatofocusing. Similarly, proteins may be separated according to hydrophobicity using hydrophobic interaction or charge induction chromatography or affinity chromatography utilizing differences in affinity towards a specific immobilized ligand or protein. Separation of complex mixtures of proteins may thus be achieved by sequential combination of various chromatographic principles. A mixture of proteins may thus initially be separated according to e.g. net charge using ion-exchange chromatography and proteins of similar net charge may subsequently be separated according to molecular weight using gelfiltration chromatography or after hydrophobicity using hydrophobic interactions chromatography in the presence of a high concentration of a selected salt.

Affinity chromatography combined with subsequent purification steps such as ion-exchange chromatography, hydrophobic interactions and gel filtration has frequently been used for the purification of IgG (polyclonal as well as monoclonal) and TcR from different sources e.g., ascites fluid, cell culture supernatants and serum. Affinity purification, where the separation is based on a reversible interaction between the protein(s) and a specific ligand coupled to a chromatographic matrix, is an easy and rapid method, which offers high selectivity, usually high capacity and concentration into a smaller volume. Protein A and protein G, two bacterial cell surface proteins, have high affinity for the $F_c$ region of antibodies, and have, in an immobilized form, been used for many routine applications, including purification of polyclonal IgG and its subclasses from various species and absorption and purification of immune complexes.

Following affinity chromatography, downstream chromatography steps, e.g. ion-exchange and/or hydrophobic interaction chromatography, can be performed to remove host cell proteins, leaked Protein A, and DNA.

Gel filtration, as a final purification step, can be used to remove contaminant molecules such as dimers and other aggregates, and transfer the sample into storage buffer. Depending on the source and expression conditions it may be necessary to include an additional purification step to achieve the required level of antibody purity. Hydrophobic interaction chromatography or ion-exchange chromatography are thus frequently used, in combination with Protein A and gel filtration chromatography, to purify antibodies for therapeutic use.

In order to ease the purification, it is preferable that all members of the polyclonal antibody share the same constant region of the heavy and/or light chain In order to purify other classes of antibodies, alternative affinity chromatography media, have to be used since proteins A and G do not bind IgA and IgM. An immunoaffinity purification can be used (anti-IgA or anti-IgM monoclonal antibodies coupled to solid phase) or, alternatively, multistep purification strategies including ion-exchange and hydrophobic interaction can be employed.

Structural Characterization

Structural characterization of polyclonal proteins such as antibodies and TcRs requires high resolution due to the complexity of the mixture (clonal diversity and glycosylation). Traditional approaches such as gel filtration, ion-exchange chromatography or electrophoresis may not have sufficient resolution to differentiate among the individual antibodies. Two-dimensional polyacrylamide gel electrophoresis (2D-PAGE) has been used for profiling of complex protein mixtures followed by mass spectrometry (MS) or liquid chromatography (LC)-MS (e.g., proteomics). 2D-PAGE, which combines separation on the basis of a protein's charge and mass, has proven useful for differentiating among polyclonal, oligoclonal and monoclonal immunoglobulin in serum samples. However, this method has some limitations. Chromatographic techniques, in particular capillary and LC coupled to electrospray ionization MS are increasingly being applied for the analysis of complex peptide mixtures. LC-MS has been used for the characterization of monoclonal antibodies. The analysis of very complex samples requires more resolving power of the chromatographic system, which can be obtained by separation in two dimensions (or more). Such an approach could be based on ion-exchange in the first dimension and reversed-phase chromatography (or hydrophobic interaction) in the second dimension optionally coupled to MS.

Functional Characterization

A polyclonal protein can for example be characterized functionally through comparability studies with polyclonal proteins with specificity towards the same target or a similar activity. Such studies can be performed in vitro as well as in vivo.

An in vitro functional characterization of a polyclonal antibody could for example be immunoprecipitation which is a highly specific technique for the analytical separation of target antigens from crude cell lysates. By combining immunoprecipitation with other techniques, such as SDS-PAGE followed by protein staining (Coomassie Blue, silver staining or biotin labeling) and/or immunoblotting, it is possible to detect and quantify antigens e.g., and thus evaluate some of the functional properties of the antibodies. Although this method does not give an estimate of the number of antibody molecules nor their binding affinities, it provides a visualization of the target proteins and thus the specificity. This method can likewise be used to monitor potential differences of the antibodies toward antigens (the integrity of the clonal diversity) during the expression process.

An in vivo functional characterization of a polyclonal antibody could for example be infection studies. An experimental animal such as a mouse can for example be infected with a specific virus, towards which a polyclonal antibody has been developed. The degree to which the infection can be inhibited will indicate functionality of the polyclonal antibody.

Therapeutic Compositions

In an embodiment of the invention, a pharmaceutical composition comprising a recombinant polyclonal protein selected from the immunoglobulin super family as it active ingredient is intended for the treatment or prevention of a disease in a mammal.

In a preferred embodiment of the present invention, the pharmaceutical composition comprises a recombinant polyclonal antibody or antibody fragment as the active ingredient and a pharmaceutically acceptable excipient.

In another preferred embodiment of the present invention, the pharmaceutical composition comprises a recombinant polyclonal T cell receptor or T cell receptor fragment as the active ingredient and a pharmaceutically acceptable excipient.

The pharmaceutical compositions of the present invention are prepared in a manner known per se, for example, by means of conventional dissolving, lyophilising, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, poly vinylpyrrolidone or gelatin.

The injection compositions are prepared in customary manner under sterile conditions; the same applies also to introducing the compositions into ampoules or vials and sealing the containers.

The pharmaceutical compositions may comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, drages, tablets or capsules.

Therapeutic Uses of the Compositions According to the Invention

The pharmaceutical compositions according to the present invention may be used for the treatment, amelioration or prevention of a disease in a mammal. Diseases that can be treated with the present pharmaceutical compositions include cancer, infectious diseases, inflammatory diseases, allergy, asthma and other respiratory diseases, autoimmune diseases, cardiovascular diseases, diseases in the central nervous system, metabolic and endocrine diseases, transplantation rejections and undesired pregnancy.

One aspect of the present invention is a method for disease treatment, amelioration or prophylaxis in an animal, wherein an effective amount of the recombinant polyclonal antibody or antibody fragment is administered. In a further aspect an effective amount of the recombinant polyclonal T cell receptor or T cell receptor fragment is administered.

An additional aspect of the present invention is the use of a recombinant polyclonal antibody or recombinant polyclonal T cell receptor or fragments of antibodies or T cell receptors for the preparation of a composition for the treatment of diseases selected from a group consisting of a cancer, an infection, an inflammatory disease, an allergy, asthma or other respiratory disease, immunological malfunctions, an autoimmune disease, a cardiovascular disease, a disease in the central nervous system, a metabolic disease, an endocrine diseases, transplant rejection, and undesired pregnancy.

Diagnostic Use and Environmental Detection Use

Another embodiment of the invention is directed to diagnostic kits and kits for environmental detection use as well as methods for using these kits. Kits according to the present invention comprise a recombinant polyclonal protein prepared according to the invention which protein may be labeled with a detectable label or non-labeled for non-label detection. If labeled, the present recombinant polyclonal protein may be added to a sample suspected of containing the target molecule and the presence or absence of the label indicate the presence or absence of the target molecule. The sample to be tested may be a sample of bodily fluid such as blood, serum, plasma, spinal fluid, lymph or urine or a non-mammalian sample such as a sample from an environmental source suspected of harboring a contaminant. Non-mammalian samples may be water, air or contaminated earth. Non-label detection encompasses the measurement of refractive change in BIAcore upon binding, wherein the recombinant polyclonal protein is used to capture the target molecule.

EXAMPLES

The following examples illustrate the invention, but should not be viewed as limiting the scope of the invention.

Example 1

Derivation of CHO Cell Clones Expressing Antibodies

Expression Vector

The IgG expression vector used is shown in FIG. 2a.
The E1A expression vector is shown in FIG. 2b.

Cell Line

The cell line used is a derivative of the DHFR-negative CHO cell line DG44 obtained from Lawrence Chasin, Columbia University (also available from Gibco cat #12613-014). DG44 cells were transfected with a cDNA for the 13S version of the adenovirus type 5 transactivator E1A (NCBI accession no. AY339865, SEQ ID NO. 1: cDNA sequence: atgagacatattatctgccacggaggtgttattaccgaagaaatgg ccgccag tcttttggaccagctgatcgaagaggtactggc tgataatcttccacctcctagc-cattttgaaccacctaccttcacgaactgtatgatttagacgtgacggccc ccgaa-gatcccaa cgaggaggcggtttcgcagattttccccgactctgtaatgttggcgg tgcaggaagggattgacttactcactttccgccggcgc ccggttctccggagc-cgcctcaccttccggcagcccgagcagccggagcagagagcc ttgggtccg-gtttcta tgccaaac cttgtaccggaggtgatcgatcttacctgccac gaggctg-gcttccac ccagtgacgacgaggatgaagagggtgaggagttt gtgtta gattatgtggagcaccccgggcacggttgcaggtcttgtcattat caccggag-gaatacgggggacccagatattatgtg ttcgctgctatatgaggacctgtggcat-gttttgtctacagtcctgtgtctgaacctgagcctgagcccgagccagaaccggagc ctgcaagacctacccgccgtcctaaaatggcgcctgcta tcctgagacgcccga-catcacctgtgtctagagaatgcaatagtag tacggatagctgtgactccggtcct-tctaacacacctcctgagatacacccggtggtcccgctgtgcccc attaaaccagt-tgccgtgagagttggtgggcgtcgccaggctgtggaatgtatc gaggactt gcttaacgagcctgggcaacctttggacttgagctgtaa acgccccaggccataa) in the vector pcDNA3.1+(Cat # V790-20, Invitrogen). Transfectants were selected with Geneticin (Invitrogen) at a concentration of 500 µg/ml. After selection the cells were single-cell cloned by limiting dilution. Clones were tested for transactivation of the CMV promoter (improved expression) by transient transfection with an antibody plasmid (shown above). A single clone showed an expression level in the transient assay that was improved by a factor of 3 compared to the untransfected DG44 cell line. The increased expression level is no evidence of actual transactivation and could be caused by selection of a particularly high expressing subclone. In comparisons performed with stable transfection, selected pools showed a 4-5 times increased expression level compared to the wild-type DG44 cell line. This clone (termed ECHO) was subcloned twice and appeared to be stable with regard to transactivation of the CMV promoter (improved expression). Actual transactivation of the CMV promoter was not measured, but the clone nevertheless showed stable high expression of antibody under the control of the CMV promoter.

Antibody Expression Plasmids

The antibody expression plasmids used were constructed as shown above. For this purpose 6 different antibodies directed against different Vaccinia virus surface proteins were chosen. They were chosen because each of them has a very characteristic profile in ion exchange chromatography making possible an identification and quantification in mixes of different antibodies. The antibodies (disclosed in co-pending PCT/DK2006/000686 filed on Dec. 4, 2006, titled "Anti-orthopoxvirus recombinant polyclonal antibody", published as WO 2007/065433) were:

Sym002-037 (clone 002-037)
Sym002-186 (clone 002-186)
Sym002-235 (clone 002-235)
Sym002-286 (clone 002-286)
Sym002-303 (clone 002-303)
Sym002-482 (clone 002-482)

IgG ELISA

IgG was measured by sandwich ELISA. Briefly, 96-well plates (Maxisorp, NUNC) were coated with goat anti-human Fc (Serotec, STAR106) followed by incubation with samples and standard (purified human monoclonal IgG1 kappa antibody). Detection was performed with goat anti-human kappa light chains conjugated with horseradish peroxidase (Serotec STAR100P).

Transfection of ECHO Cells

ECHO cells were seeded in T80 flasks at a density of $0.30*10^6$ cells/per flask in MEM alpha medium with nucleosides (Invitrogen cat. no. 32571) with 10% fetal calf serum (FCS) (Invitrogen). Within an hour from seeding, the cells were transfected with Fugene6 (Roche):

10 µl of Fugene6 is mixed with 490 µl Dulbecco's modified Eagle's medium and allowed to incubate for 5 min. at room temperature 5 µg of expression plasmid is added and the mix is incubated for a further 15 min. at room temperature The mix is added to the cell culture flask On the following day the medium with transfection reagents was aspirated, each flask was washed once with 5 ml of MEM alpha medium (without nucleosides) with 10% dialyzed FCS (Invitrogen) (MEMalpha-) and 10 ml of the same medium was added together with methotrexate at a concentration of 2 nM. Following this the medium was changed twice a week.

After 15 days the cells were trypsinized and all cells were transferred to new flasks. After a further 2 days of culture the medium was changed and the following day the medium was aspirated, the cells were counted and productivities were measured in IgG ELISA. The results are shown in Table 3. Productivities are calculated as picograms per cell per day using the cell number at the time of harvest.

TABLE 3

Cell counts, IgG content of medium and specific cellular productivities of transfected pools

| Antibody | IgG conc., µg/ml | Total IgG | Cell number, $*10^6$ | Productivity, picograms per cell per day |
|---|---|---|---|---|
| Sym002-037 | 3.65 | 36.5 | 3.0 | 12.2 |
| Sym002-186 | 8.15 | 81.5 | 6.0 | 13.6 |
| Sym002-235 | 5.71 | 57.1 | 3.3 | 17.3 |
| Sym002-286 | 1.39 | 13.9 | 0.8 | 17.4 |
| Sym002-303 | 11.4 | 114 | 9.4 | 12.1 |
| Sym002-482 | 17.0 | 170 | 12.5 | 13.6 |

For the production of single-cell clones the cells in the pools were stained for surface-associated antibody and single-cell sorted into 96-well plates containing 50% ECHO-cell conditioned medium (MEMalpha-) and 50% of the same medium without conditioning. Briefly, the staining protocol was as follows:

1. Cells are trypsinized and counted
2. Pipet 1–5×10$^6$ cells into sterile FACS tube
3. Spin down cells for 1 min at 250 g 4° C. and remove supernatant
4. Wash cells in 2 ml sterile FACS PBS (PBS+2% FCS) (5 ml)
5. Stain cells with (Goat F(ab)2 fragment anti-human IgG H+L-PE (Beckman-Coulter, IM1626) diluted 1:20 in 100 µl diluted Ab/10$^6$ cells and incubate for 20 min (4° C. in the dark)
6. Wash cells twice in 2 ml FACS PBS (5 ml)
7. Resuspend to 1–5×10$^6$/ml in FACS PBS (2 ml)
8. Add propidium iodide, 10 µg/ml 1:100

A proper gate was set and cells were single-cell sorted into 96-well plates (5 plates per antibody) using a FACS-Aria (Beckton-Dickinson).

After approximately 1 week wells were inspected by microscope for the presence of single clones.

After approximately 2 weeks supernatants from wells with a single clone were assayed each in a single dilution by ELISA and based on the ELISA value and visual inspection of the wells 24 clones representing each antibody were selected for continued culture. Clones were selected using visual inspection for cell number and morphology combined with a selection for antibody expression level. Selected clones were further tested in an exhaustion assay: briefly, cells were seeded into 24-well plates and allowed to grow until most cells were dead. Supernatants were assayed by ELISA and the top 10 clones for each antibody were selected for adaptation to serum-free suspension culture.

Adaptation to Serum-Free Suspension Culture

Cells were trypsinized and counted. 5*10$^6$ cells were centrifuged and resuspended in 10 ml ProCHO4 serum-free medium (Cambrex). The cells were transferred to 50 ml cell culture tubes (TRP, Switzerland) and incubated on a shaker at 37° C. Cell densities were counted twice a week and each time the cultures were diluted to 0.5*10$^6$ cells per ml (for the first 2 weeks) or to 0.3*10$^6$ cells per ml (for the remaining period). After 4-5 weeks doubling time for most clones were approaching 30 hrs. at which time point it was considered that they were adapted to serum-free culture.

At the end of the adaptation period the cells were assayed by ELISA, frozen down in culture medium with 10% DMSO and used for expression experiments (see Example 2 below).

Example 2

Expression Experiments

To test compositional stability of mixed cultures over long time a number of mixes of clones were prepared. Based on countings made during the adaptation period doubling time was taken into consideration to the extent possible. Care was taken to match clones with similar doubling time. Altogether 9 mixes were prepared:

Mixes 1-5: in each of these was used a single clone for each antibody

Mix 6: two clones were used for each antibody

Mix 7: five clones were used for each antibody

Mix 8: 3 clones were used for each antibody

Mix 9: all available clones were used, 5-7 for each antibody

Clones were mixed so that the number of cells representing each antibody (for each antibody from 1-7 clones) constituted 1/6 of the total number of cells in the mix.

The experiment was performed in 50 ml culture tubes as described in example 1. The medium used was ProCHO4 and the total culture volumes were 10 ml. The experiment was started with a concentration of 0.3*10$^6$ cells per ml. The cultures were diluted to 0.3*10$^6$ cells per ml twice a week with 3 and 4 day intervals. Once a week samples for ELISA and ion exchange chromatography analysis were taken. The first samples were taken on day 4 and the last on day 35.

ELISA values for the 9 mixes are shown in FIG. 3.

The calculated number of cell divisions from start to finish differed in the mixes from approximately 25 to approximately 27. This means that if the cultures were diluted as described twice a week but keeping the whole volume at each point total volumes in the end would have varied between 43,000 and 152,000 liters. Large scale mammalian cell cultures in the industry are typically up to 15,000 liter which means that the mixing experiments described here as far as time of culture and number of generations is a fair simulation of culture in industrial scale.

It appears that the cellular productivity is relatively constant over the 5 week period with a tendency towards a decline in some mixes.

Analysis of IgG Composition 5-10 ml 0.22 µm filtered medium supernatant was loaded onto a 1 ml MabSelect Sure column (GE Healthcare). The column was washed with 10 ml PBS pH 7.4 and eluted with 0.1 M glycine pH 2.7 as described by the manufacturer. Pooled protein material was dialyzed twice against 40 mM NaCl, 50 mM Na-acetate pH 5.0 and total IgG concentration determined by measuring the absorbance at 280 nm.

60 μg IgG mixture was loaded onto the weak cat-ion exchange column PolyCat A (100×4, 6 mm, 3 μm, 1500 Å) from PolyLC. The protein was eluted by applying a gradient from 150 to 500 mM NaCl in a Na-Acetate pH 5.0 buffer at a flow of 1 ml/min over 72 minutes. The 215 nm absorbance of the eluate was monitored and relative amounts of individual IgGs determined by integration of the signal.

In FIG. 3 is shown the chromatograms of the cation exchange analysis of IgG composition of the first and last harvest from Mix 8 after MabSelect purification. As can be seen the individual Abs are well separated, with baseline separation of four of them. Therefore, integration of the UV signal gives a very accurate determination of relative IgG concentrations in the sample.

All mixes were analysed as described above and the content of each antibody in each mix was calculated.

A rather uniform distribution among the 6 different antibodies is seen in the start samples. The differences seen may reflect different expression level between the clones used in the mixes. The antibody content of each sample is shown graphically in FIG. 5. Surprisingly, all antibodies can clearly be identified in all the last samples. It is also seen that in mixes with more than a single clone representing each antibody (mixes 6-9) there is a tendency towards a more uniform distribution of the antibodies in the last samples.

Example 3

Expression of E1A in ECHO

To investigate the expression of E1A in ECHO the level of E1A mRNA was determined by quantitative reverse transcribed Real-Time PCR (qRT-PCR) with SYBR green. The qRT-PCR method is based on PCR amplification of a target sequence. The PCR is performed in the presence of the DNA binding dye, SYBR green that emits green light when bound to double stranded DNA. This allows for the real-time quantification of double stranded DNA after each amplification round.

When the amount of double stranded DNA is low, at the beginning of the PCR, the signal from the bound SYBR green dye cannot be distinguished from background noise. However during the amplification process the signal increases above the noise and the production of double stranded DNA can be followed. In this manner the relative amount of target initially present in the samples can be determined based on the cycles needed for the SYBR green signal to cross a specific threshold. The exact point in which the threshold is reached is the Ct value, which can be used for relative comparisons of initial target amount.
Materials and Methods Total RNA was extracted from 3.0E+06 ECHO and Hek293 cells using the RNeasy Mini Kit cat. no. 74104 from Qiagen as recommended by the manufacturer. The concentrations and integrity of the RNA samples were determined using the 2100 Bioanalyzer from Agilent with the Eukaryote Total RNA Nano Series II assay. The integrity is determined as an RNA Integrity number (RUN) between 1-10 with 1 being degraded and 10 being intact RNA. The ECHO RNA had a RIN of 9.5 and HEK293 had a RIN of 8.9. cDNA of each sample was made using the QuantiTect Reverse Transcription Kit cat. no. 205311 from Qiagen using 800 ng RNA as starting material. The Hek293 cDNA was diluted 25×, while the ECHO cDNA was diluted twice. The qRT-PCR was performed on a Stratagene Mx3005P using the Brilliant SYBR Green QPCR Master Mix cat. no. 600548 from Stratagene. Thermal cycling conditions: 10 min hold at 95° C.; 40 cycles with 15 s denaturation at 95° C., 1 min annealing at 60° C. and 30 s extension at 72° C.; melting curve analysis from 55-95° C. The primers used (SEQ ID NO. 2: E1A-696 bpF: 5'-TGACTCCGGTCCTTCTAACACA-'3, SEQ ID NO. 3: E1A-772 bpR: 5'-TCACGGCAACTGGTTTAATGG-'3) target a 77 bp fragment in the 3' end of the E1A gene.
Results The expression of E1A in ECHO cells was analyzed using the qRT-PCR assay and showed that E1A mRNA cannot be amplified and detected in this assay, strongly indicating that the ECHO cell line does not express the E1A protein. As a positive control was used the human 293 cell line which is transformed by a fragment of adenovirus DNA and known to express E1A at a relatively high level.

The qRT-PCR shows amplification in the Hek293 sample, the positive control Ct=18.74, but no amplification was seen neither in the NTC (No template control) nor in the ECHO sample.

| Sample | Ct |
|---|---|
| Hek293 | 18.74 |
| ECHO | No Ct |
| NTC | No Ct |

Example 4

Preparation of Cell Banks for Bioreactor Experiments

To be able to perform bioreactor experiments for the study of compositional stability master and working cell banks were prepared. For the experiment, clones of ECHO cell expressing 6 different antibodies as described in Example 1 were used. The clones used had been adapted to serum-free suspension culture in the culture medium ProCHO4.
Master Cell Bank Clones were thawed and allowed to recover in suspension culture for a period. 4 mixed Master Cell Banks were prepared from cells in exponential growth according to the following specifications:

Cells were frozen down when they were in logarithmic growth

All 6 antibodies were represented in each cell bank

Equal cell numbers representing each antibody were mixed

Mix 1 A-3 A contained a single clone per antibody

Mix 4 A contained 3 clones per antibody 10 ampoules each containing $20*10^6$ cells were frozen per mix Freezing medium: culture medium (ProCHO4) with 10% DMSO Working Cell Bank One frozen ampoule per mix was thawed. The mixes were kept in culture for 8-10 days before preparation of working cell bank:

Cells were frozen down when they were in logarithmic growth 10 ampoules each containing $20*10^6$ cells were frozen per mix Freezing medium: culture medium (ProCHO4) with 10% DMSO

Example 5

Compositional Stability in Bioreactor

One frozen ampoule per mix of the working cell bank was thawed and the cells were kept in culture as seed train for 14 days at which time point bioreactor culture was started:

Each seed train was used to inoculate two bioreactors with $0.6*10^6$ cells/ml in 250 ml start medium (ProCHO4+5 mM glutamine+1/100 non-essential amino acids).

The cultivations were fed from day 2 to day 14 after inoculation with feed medium (ProCHO4+6 g/L glucose+5 mM glutamine+1/100 non essential amino acids) resulting in a volume of ~585 ml at harvest day 16.

The following parameters were controlled in the DASGIP bioreactors (unit 1-8):

TABLE 4

| General bioreactor process parameters. | |
|---|---|
| Volume | 250 ml fed continuously, start day 2 until day 14 |
| Temp. set point: | 36.8° C., Shift to 32.0° C. at 120 hours |
| pH set point: | 6.95 |
| pH control: | Sterile filtered 0.25 M $Na_2CO_3$ is used. |
| Agitation: | 80 rpm. |
| $pO_2$ set point: | 30% (regulated via $O_2$-content of gas) |
| Gas flow: | 0.1 sl/h |
| $CO_2$-level: | Adjusted by DASGIP system in order to keep pH |

Every day 5 ml samples were taken for analysis of viability, viable cell number, IgG production and metabolites. All cultures performed as expected with viabilities and viable cell numbers, which were alike. Further 10 ml was taken for analysis of the IgG composition by ion exchange chromatography analysis from the seed train (at day 9 and day 14) and from each bioreactor (unit 1-8) at day 20, day 24, day 28 and day 30 after thaw of the ampoules.

The analysis of the IgG composition was performed as described under example 2 above.

All mixes were analysed as described above and the content of each antibody in each sample of the 4 mixes was calculated. The total yield of IgG from the cultures ranged from approximately 150 to 250 mg/L.

The antibody content of each sample is shown graphically in 5. Surprisingly, all antibodies can clearly be identified in all samples. The composition appears robust none of the clones are lost or has taken over during a 14 days seed train cultivation followed by a 16 days bioreactor run. The compositions are different depending on the input clones.

It also appears possible by selecting specific clones for a mixture to determine the relative distribution of the individual antibodies in the final product.

The invention claimed is:

1. A method for generation of a polyclonal cell line capable of expressing a polyclonal protein comprising 2 to n distinct members, said method comprising:
   a) providing a set of expression vectors, wherein each of said vectors comprises at least one copy of a distinct nucleic acid encoding a distinct member of said polyclonal protein;
   b) separately transfecting host cells with one of said expression vectors under conditions avoiding site-specific integration of the expression vectors into the genome of the cells, thereby obtaining 2 to n compositions of cells, each composition expressing one distinct member of the polyclonal protein; and
   c) mixing said 2 to n compositions of cells to obtain a polyclonal cell line.

2. The method according to claim 1, wherein the expression vectors are episomal vectors.

3. The method of claim 1, wherein the expression vectors are stably and randomly integrated into one or more chromosomes of the host cells.

4. The method according to claim 1, wherein the transfected cells obtained in step b) are cloned.

5. The method of claim 4, wherein the cells are cloned using FACS cloning.

6. The method of claim 4, wherein clones are selected for at least one criterion selected from the group consisting of: growth rate, doubling time, expression level, production level, stability of production over time, viability, hardiness, robustness, morphology, and copy number.

7. The method of claim 6, wherein clones are selected for uniformity with respect to the at least one criterion.

8. The method of claim 7, comprising selecting for uniformity with respect to doubling time and expression level.

9. The method of claim 4, wherein more than one clone is selected for each distinct polyclonal protein member.

10. The method of claim 9, wherein 2 clones are selected for each distinct polyclonal protein member, or wherein 3, 4, 5, 6, 7, 8, 9, 10, 11, 12, 13, 14, 15, 16, 17, 18, 19, 20, 25, 30, 35, 40, 45, 50, 60, 70, 80, 90, or 100 clones are selected.

11. The method according to claim 1, where said compositions of cells expressing different distinct members are mixed in a 1:1 ratio.

12. The method according to claim 1, wherein said compositions of cells are mixed in a ratio different from a 1:1 ratio.

13. The method of claim 1, wherein the expression vectors are identical except for variations in the coding sequence of the polyclonal protein.

14. The method of claim 1, wherein the host cells are derived from one clone prior to transfection.

15. The method of claim 1, wherein the polyclonal protein is a multimeric protein.

16. The method of claim 15, wherein one expression vector encodes all subunits of one distinct polyclonal protein member.

17. The method of claim 15, wherein the set of expression vectors in step a) comprises two or more subsets of expression vectors, where a first subset comprises nucleic acid sequences encoding one subunit of the multimeric protein, and a second subset comprises nucleic acid sequences encoding another subunit of the multimeric protein, such that each transfection is performed with a member of the first subset and a member of the second subset of expression vectors.

18. The method of claim 1, wherein the expression vector or a further expression vector encodes a selectable marker.

19. The method of claim 18, wherein cells are continuously cultured under conditions favoring growth of cells expressing the selectable marker.

20. The method of claim 18, wherein the selectable marker comprises a gene product in which the host cell is deficient.

21. The method of claim 18, wherein the selectable marker is encoded by a transcript that also encodes a polypeptide member or a subunit of said polypeptide member.

22. The method according to claim 1, wherein the polyclonal protein is not naturally associated with the host cells.

23. The method according to claim 1, wherein the polyclonal protein is a recombinant polyclonal antibody or a recombinant polyclonal antibody fragment.

24. The method according to claim 23, wherein the set of expression vectors in step a) comprises two subsets of expression vectors, where the first subset comprises nucleic acid sequences encoding an antibody heavy chain, and the second subset comprises nucleic acid sequences encoding an antibody light chain, such that each transfection is performed with a member of the first subset and a member of the second subset of expression vectors.

25. The method of claim 23, wherein the recombinant polyclonal antibodies have the same constant region of the heavy or light chain.

26. The method according to claim 1, wherein the polyclonal protein is a polyclonal T cell receptor or a polyclonal T cell receptor fragment.

27. The method of claim 1, wherein the host cells are prokaryotic.

28. The method of claim 1, wherein the host cells are eukaryotic.

29. The method of claim 28, wherein the eukaryotic cells are selected from the group consisting of plant, yeast, fungus, vertebrate, or invertebrate cells.

30. The method of claim 28, wherein the eukaryotic cells are selected from the group consisting of Chinese hamster ovary (CHO) cells, COS cells, BHK cells, myeloma cells, NIH 3T3, fibroblasts and immortalised human cells.

31. The method of claim 28, wherein the host cell expresses a recombinant transactivator, capable of transactivating the promoter coding for expression of the polyclonal protein.

32. A method for manufacture of a polyclonal protein, said method comprising:
a) providing a polyclonal cell line obtained using the method of claim 1;
b) culturing the polyclonal cell line under conditions allowing for expression of the polyclonal protein; and
c) recovering and optionally purifying the polyclonal protein from the cells or medium.

33. The method of claim 32, wherein one polyclonal cell line expressing one population of distinct members of the polyclonal protein is cultured in one container, and at least a second polyclonal cell line expressing a second population of distinct members of the polyclonal protein is cultured in a second container, and the polyclonal protein from each container is mixed prior to or after purification.

34. The method of claim 32, further comprising a step to verify the presence of each of the distinct members in the recovered and optionally purified polyclonal protein.

35. A polyclonal cell line comprising 2 to n populations of cells, wherein each population expresses a distinct member of a recombinant polyclonal protein, and wherein each cell comprises at least one expression construct randomly integrated into the genome of said cell such that the integration sites vary between members of the polyclonal cell line.

36. The polyclonal cell line of claim 35, wherein the at least one expression construct is integrated into one or more chromosomes.

37. The polyclonal cell line of claim 35, wherein n is 3 or more.

38. The polyclonal cell line of claim 35, wherein n is less than 50.

39. The polyclonal cell line of claim 35, wherein cells expressing one distinct member of the recombinant polyclonal protein are derived from a single cloned cell.

40. The polyclonal cell line of claim 35, wherein the polyclonal protein is a multimeric protein.

41. The polyclonal cell line of claim 40, wherein each expression construct encodes the subunits of a multimeric protein.

42. The polyclonal cell line of claim 40, wherein expression of the subunits is under the control of the same or identical promoters.

43. The polyclonal cell line of claim 35, wherein the expression constructs encode a selectable marker.

44. The polyclonal cell line of claim 43, wherein the selectable marker is encoded by a transcript that also encodes a polypeptide member or a subunit of said polypeptide member.

45. The polyclonal cell line of claim 35, wherein the polyclonal protein is not naturally associated with the cells.

46. The polyclonal cell line of claim 35, wherein the polyclonal protein is a recombinant polyclonal antibody or a recombinant polyclonal antibody fragment.

47. The polyclonal cell line of claim 46, wherein all members of the polyclonal antibody are of the same isotype.

48. The polyclonal cell line of claim 35, wherein the polyclonal protein is a polyclonal T cell receptor or a polyclonal T cell receptor fragment.

49. The polyclonal cell line of claim 35, wherein the cells are prokaryotic.

50. The polyclonal cell line of claim 35, wherein the hoot cells are eukaryotic.

51. The polyclonal cell line of claim 35, wherein the cells comprise a stably integrated expression construct coding for a transactivator capable of transactivating the promoter coding for the members of the polyclonal protein.

52. The method of claim 1, wherein n is less than 30.

53. The method of claim 31, wherein the recombinant transactivator is an adenovirus type 5 transactivator E1A operably linked to a constitutive promoter.

54. The method of claim 53, wherein the promoter is a CMV promoter.

55. The polyclonal cell line of claim 35, wherein cells expressing one distinct member of the recombinant polyclonal protein are derived from at least two cloned cells.

56. The polyclonal cell line of claim 38, wherein n is less than 30.

57. The polyclonal cell line of claim 51, wherein the transactivator is an adenovirus type 5 transactivator E1A operably linked to a constitutive promoter.

58. The polyclonal cell line of claim 57, wherein the promoter is a CMV promoter.

59. A polyclonal cell line comprising 2 to n populations of cells, wherein each population expresses a distinct member of a recombinant polyclonal antibody or a binding fragment thereof, and wherein each cell comprises expression constructs for expression of one antibody molecule or binding fragment randomly integrated into the genome of said cell such that the integration sites vary between members of the polyclonal cell line.

* * * * *

UNITED STATES PATENT AND TRADEMARK OFFICE
CERTIFICATE OF CORRECTION

| | | |
|---|---|---|
| PATENT NO. | : 7,910,332 B2 | Page 1 of 1 |
| APPLICATION NO. | : 12/153809 | |
| DATED | : March 22, 2011 | |
| INVENTOR(S) | : Nielsen et al. | |

It is certified that error appears in the above-identified patent and that said Letters Patent is hereby corrected as shown below:

<u>Column 44</u>
Lines 25-26, please replace "wherein the hoot cells are eukaryotic." with --wherein the cells are eukaryotic.--

Signed and Sealed this
Seventh Day of June, 2011

David J. Kappos
*Director of the United States Patent and Trademark Office*